US012702631B2

(12) United States Patent
Baig et al.

(10) Patent No.: US 12,702,631 B2
(45) **Date of Patent: *Aug. 11, 2026**

(54) ORAL CARE COMPOSITIONS COMPRISING HOPS BETA ACIDS AND FLUORIDE IONS

(71) Applicant: The Procter & Gamble Company, Cincinnati, OH (US)

(72) Inventors: Arif Ali Baig, Mason, OH (US); Tammy Baker, Cincinnati, OH (US); Aaron Reed Biesbrock, Maineville, OH (US); Samuel James St. John, Cincinnati, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 19/230,165

(22) Filed: Jun. 6, 2025

(65) Prior Publication Data

US 2025/0295565 A1 Sep. 25, 2025

Related U.S. Application Data

(63) Continuation of application No. 18/322,979, filed on May 24, 2023, now Pat. No. 12,350,355, which is a continuation of application No. 17/037,766, filed on Sep. 30, 2020, now Pat. No. 11,696,881.

(60) Provisional application No. 62/994,893, filed on Mar. 26, 2020, provisional application No. 62/985,451, filed on Mar. 5, 2020, provisional application No. 62/972,111, filed on Feb. 10, 2020, provisional application No. 62/972,109, filed on Feb. 10, 2020, provisional application No. 62/943,940, filed on Dec. 5, 2019, provisional application No. 62/907,733, filed on Sep. 30, 2019, provisional application No. 62/907,736, filed on Sep. 30, 2019, provisional application No. 62/907,735, filed on Sep. 30, 2019.

(51) Int. Cl.

| | |
|---|---|
| ***A61K 8/27*** | (2006.01) |
| ***A61K 8/20*** | (2006.01) |
| ***A61K 8/21*** | (2006.01) |
| ***A61K 8/24*** | (2006.01) |
| ***A61K 8/35*** | (2006.01) |
| ***A61K 8/362*** | (2006.01) |
| ***A61K 8/365*** | (2006.01) |
| ***A61K 8/44*** | (2006.01) |
| ***A61K 8/73*** | (2006.01) |
| ***A61K 8/81*** | (2006.01) |
| ***A61K 8/97*** | (2017.01) |
| ***A61K 8/9789*** | (2017.01) |
| ***A61K 36/185*** | (2006.01) |
| ***A61Q 11/00*** | (2006.01) |

(52) U.S. Cl.

CPC ................. *A61K 8/27* (2013.01); *A61K 8/20* (2013.01); *A61K 8/21* (2013.01); *A61K 8/24* (2013.01); *A61K 8/35* (2013.01); *A61K 8/362* (2013.01); *A61K 8/365* (2013.01); *A61K 8/44* (2013.01); *A61K 8/731* (2013.01); *A61K 8/8147* (2013.01); *A61K 8/97* (2013.01); *A61K 8/9789* (2017.08); *A61K 36/3486* (2024.05); *A61Q 11/00* (2013.01); *A61K 2800/28* (2013.01); *A61K 2800/30* (2013.01); *A61K 2800/48* (2013.01); *A61K 2800/74* (2013.01); *A61K 2800/92* (2013.01)

(58) Field of Classification Search

CPC ... A61K 8/27; A61K 8/19; A61K 8/20; A61K 8/21; A61K 8/24; A61K 8/35; A61K 8/355; A61K 8/362; A61K 8/365; A61K 8/44; A61K 8/731; A61K 8/8147; A61K 8/97; A61K 8/9789; A61K 36/3486; A61K 2800/28; A61K 2800/30; A61K 2800/48; A61K 2800/74; A61K 2800/92; A61Q 11/00

See application file for complete search history.

(56) References Cited

U.S. PATENT DOCUMENTS

| | | | |
|---|---|---|---|
| 2,723,217 | A | 11/1955 | Gershon |
| 3,431,339 | A | 3/1969 | Gyarmathy et al. |
| 3,471,613 | A | 10/1969 | Gagolski |
| 3,624,120 | A | 11/1971 | Yetter |
| 3,639,570 | A | 2/1972 | Grand |
| 3,914,404 | A | 10/1975 | Langer |
| 3,925,556 | A | 12/1975 | Bauman |
| 3,932,603 | A | 1/1976 | Haas |
| 3,953,605 | A | 4/1976 | Bauman |
| 3,956,479 | A | 5/1976 | Bauman |

(Continued)

FOREIGN PATENT DOCUMENTS

| | | | |
|---|---|---|---|
| CN | 101123943 | A | 2/2008 |
| CN | 102811698 | A | 12/2012 |

(Continued)

OTHER PUBLICATIONS

"BetaBio 45%", XP055755137, Retrieved from the Internet:URL:https://www.hopsteiner.com/wp-content/uploads/2019/07/25_09_BetaBio-45.pdf; Jul. 1, 2019, 3 pages.

(Continued)

*Primary Examiner* — Lezah Roberts

(74) *Attorney, Agent, or Firm* — John G. Powell

(57) ABSTRACT

Oral care compositions with an anticaries or anticavity effect. Oral care compositions that have an extract from a species in the Humulus family and an anticaries drug, such as a fluoride ion source. Oral care compositions have fluoride and hops beta acid, such as from an extract from *Humulus lupulus*. Oral care compositions have a fluoride ion source and a hops beta acid derived from an extract of *Humulus lupulus*.

16 Claims, No Drawings

(56) References Cited

U.S. PATENT DOCUMENTS 3,985,869 A 10/1976 Yoshimura
4,022,880 A 5/1977 Vinson
4,042,680 A 8/1977 Muhler
4,048,299 A 9/1977 Litchfield
4,088,752 A 5/1978 Muhlemann
4,108,981 A 8/1978 Muhler
4,132,773 A 1/1979 Best
4,154,813 A 5/1979 Kleinberg
4,166,073 A 8/1979 Bauman
4,235,875 A 11/1980 Abramo
4,416,867 A 11/1983 Ritchey et al.
4,435,381 A 3/1984 Flagg
4,438,093 A 3/1984 Shimada
4,618,489 A 10/1986 Pollock
4,737,359 A 4/1988 Eigen
4,976,954 A 12/1990 Kleber
5,064,640 A 11/1991 Kleber
5,281,410 A 1/1994 Lukacovic
5,370,863 A 12/1994 Barney
5,525,330 A 6/1996 Gaffar
5,531,982 A 7/1996 Gaffar
5,534,243 A 7/1996 Dixon, Jr.
5,741,487 A 4/1998 Asai
5,762,911 A 6/1998 Kleinberg
5,770,588 A 6/1998 Mcnamara
5,961,958 A 10/1999 Homola
6,129,907 A 10/2000 Sreenivasan
6,136,298 A 10/2000 Gaffar
6,165,447 A 12/2000 Trivedi
6,180,599 B1 1/2001 Min
6,207,138 B1 3/2001 Zhang
6,241,974 B1 6/2001 White, Jr. et al.
6,471,946 B1 10/2002 Takatsuka et al.
6,475,537 B1 11/2002 King et al.
6,521,216 B1 2/2003 Glandorf et al.
6,607,711 B2 8/2003 Pedersen
6,846,478 B1 1/2005 Doyle et al.
7,910,139 B2 3/2011 Bombardelli
7,910,140 B2 3/2011 Wilson
8,071,136 B2 12/2011 Kuhrts
8,283,135 B2 10/2012 Doyle
8,652,495 B2 2/2014 Porter
8,691,190 B2 4/2014 Haught
8,900,644 B2 12/2014 Trivedi
9,119,879 B2 9/2015 Du-thumm
9,192,589 B2 11/2015 Subramanyam
9,532,932 B2 1/2017 Prencipe
9,855,200 B2 1/2018 Campbell et al.
9,883,995 B2 2/2018 Prencipe
10,105,303 B2 10/2018 Pan
10,596,088 B2 3/2020 Strand
10,596,089 B2 3/2020 Strand
10,603,263 B2 3/2020 Strand
11,918,681 B2 3/2024 Shi
2003/0003059 A1 1/2003 Dana
2003/0003069 A1 1/2003 Carson et al.
2003/0095931 A1 5/2003 Stier
2003/0157145 A1 8/2003 Kalili
2003/0165442 A1 9/2003 Baig
2004/0037790 A1 2/2004 Watanabe
2004/0042978 A1 3/2004 Embro
2004/0057908 A1 3/2004 Bowen
2004/0175480 A1 9/2004 Seman et al.
2005/0025720 A1 2/2005 Bailey
2006/0127343 A1 6/2006 Bernard et al.
2006/0134020 A1 6/2006 Robinson et al.
2006/0134024 A1 6/2006 Trivedi et al.
2006/0198849 A1 9/2006 Paau
2007/0092456 A1 4/2007 Inaba
2007/0248549 A1 10/2007 Kuhrts
2008/0003186 A1 1/2008 Imai
2008/0193531 A1 8/2008 Hermelin
2008/0219964 A1 9/2008 Keefe et al.
2009/0186090 A1 7/2009 Zaidel
2009/0202450 A1 8/2009 Prencipe
2009/0202451 A1 8/2009 Prencipe
2010/0158840 A1 6/2010 Hiramoto
2010/0316580 A1 12/2010 Kohli
2010/0322987 A1 12/2010 Robinson
2010/0322988 A1 12/2010 Prencipe
2010/0330003 A1 12/2010 Robinson
2011/0039927 A1 2/2011 Madsen et al.
2011/0052509 A1 3/2011 Subramanyam
2012/0207676 A1 8/2012 Gruaz-guyon
2012/0237455 A1 9/2012 Trivedi et al.
2012/0237456 A1 9/2012 Trivedi et al.
2012/0244086 A1 9/2012 Trivedi et al.
2012/0244087 A1 9/2012 Trivedi et al.
2013/0142736 A1 6/2013 Robinson
2013/0287709 A1 10/2013 Maloney
2015/0297477 A1 10/2015 Poth
2015/0297500 A1 10/2015 Robinson
2015/0306015 A1 10/2015 Lin et al.
2015/0313813 A1 11/2015 Rege
2015/0320654 A1 11/2015 Li et al.
2016/0250122 A1 9/2016 Lin et al.
2016/0324738 A1 11/2016 Baig
2016/0324741 A1 11/2016 Baig
2017/0020801 A1 1/2017 Santarpia
2017/0056531 A1 3/2017 Shi
2017/0100312 A1 4/2017 Prencipe
2017/0319444 A1 11/2017 Dehghan
2017/0348206 A1 12/2017 Vemishetti
2017/0348550 A1 12/2017 Josias
2017/0367947 A1 12/2017 Rege et al.
2018/0028417 A1 2/2018 Koo
2018/0028423 A1 2/2018 Thomson et al.
2018/0072944 A1 3/2018 Shi
2018/0168960 A1 6/2018 Manus et al.
2019/0175466 A1 6/2019 Fei et al.
2019/0298620 A1 10/2019 Strand
2019/0298634 A1 10/2019 Strand
2019/0298635 A1 10/2019 Strand
2019/0298636 A1 10/2019 Strand
2021/0093525 A1 4/2021 Baig et al.
2021/0093528 A1 4/2021 St. John et al.
2021/0093549 A1 4/2021 Baig et al.
2021/0093550 A1 4/2021 Baig et al.
2021/0093551 A1 4/2021 Baig et al.
2021/0121392 A1 4/2021 Shi et al.
2022/0304918 A1 9/2022 Baig et al.
2022/0304919 A1 9/2022 St. John
2022/0313595 A1 10/2022 Baig et al.
2023/0293401 A1 9/2023 Baig
2023/0310287 A1 10/2023 Baig
2024/0156715 A1 5/2024 Shi
2024/0299264 A1 9/2024 Baig
2024/0382396 A1 11/2024 Baig
2025/0009617 A1 1/2025 St. John et al.

FOREIGN PATENT DOCUMENTS

CN 106075545 A 6/2016
CN 106029175 A 10/2016
CN 106309215 A 1/2017
CN 106309629 A 1/2017
CN 106389138 A 2/2017
CN 106937921 A 7/2017
CN 107468587 A 12/2017
CN 108938544 A 12/2018
EP 0311260 B1 12/1994
EP 0875238 A2 11/1998
EP 0740932 B1 9/2002
EP 1185237 B1 9/2003
EP 1200053 B1 12/2005
EP 1203575 B1 9/2010
EP 1843741 B1 4/2013
EP 2753292 B1 6/2018
GB 1115370 A 5/1968
GB 1130566 A 10/1968
GB 1355233 A 6/1974
JP S5326331 A 3/1978
JP S63211219 A 9/1988
JP 2001504083 A 3/2001

(56) References Cited

FOREIGN PATENT DOCUMENTS

| | | | |
|---|---|---|---|
| JP | 2001258502 | A | 9/2001 |
| JP | 2008143870 | A | 6/2008 |
| JP | 2009514789 | A | 4/2009 |
| JP | 4347161 | B2 | 7/2009 |
| JP | 2011063556 | A | 3/2011 |
| JP | 2011088939 | A | 5/2011 |
| JP | 2013512905 | A | 4/2013 |
| JP | 2013523730 | A | 6/2013 |
| JP | 2014221781 | A | 11/2014 |
| JP | 2015521604 | A | 7/2015 |
| JP | 2015155438 | A | 8/2015 |
| JP | 2016516777 | A | 6/2016 |
| JP | 2018091028 | A | 6/2018 |
| JP | 2019052186 | A | 4/2019 |
| KR | 20110133194 | A | 12/2011 |
| WO | 9107163 | A1 | 5/1991 |
| WO | 9909842 | A1 | 3/1999 |
| WO | 0110401 | A1 | 2/2001 |
| WO | 2006027248 | A2 | 3/2006 |
| WO | 2006040189 | A1 | 4/2006 |
| WO | 2007012080 | A3 | 5/2007 |
| WO | 2007061796 | A2 | 5/2007 |
| WO | 2008041055 | A1 | 4/2008 |
| WO | 2008065875 | A1 | 6/2008 |
| WO | 2011053291 | A1 | 5/2011 |
| WO | 2012057739 | A1 | 5/2012 |
| WO | 2012087288 | A2 | 6/2012 |
| WO | 2015171836 | A1 | 11/2015 |
| WO | 2015171837 | A1 | 11/2015 |
| WO | 2019183888 | A1 | 10/2019 |
| WO | 2022067140 | A1 | 3/2022 |
| WO | 2022067141 | A1 | 3/2022 |
| WO | 2022067142 | A1 | 3/2022 |

OTHER PUBLICATIONS

"GNPD—Maximum Bio-Active Super Fresh Toothpaste", XP055186450, Retrieved from the Internet: URL: http://www.gnpd.com/sinatra/recordpage/2337697/from_search/IQ5ZuZM2pG/, Mar. 1, 2014, 2 Pages.
0ral Care, Honeywell Fine Chemicals, Retrieved from URL: https://www.additiveschemicals-honeywell.com/finechemicals/applications/personal-care/oral-care/, Nov. 30, 2020, pp. 1-3.
PCT Search Report and Written Opinion for PCT/US2020/070597 dated Dec. 14, 2020, 13 pages.
Agarwal et al., "Prevention of Dental Caries-Measures beyond Fluoride.", In Journal of Oral Hygiene & Health, vol. 2, Issue 1, Mar. 3, 2014, 6 Pages.
Akande, O.O. et al., "A Laboratory Evaluation of the Efficacy of a Herbal Dentifrice on Dental Caries in the Rat", African J of Bio Res, vol. 7, 2004, pp. 89-92.
All Office Actions: U.S. Appl. No. 18/418,609, filed Jan. 22, 2024; See Patent Center.
All Office Actions; U.S. Appl. No. 17/037,766, filed Sep. 30, 2020; See Patent Center.
All Office Actions; U.S. Appl. No. 17/037,773, filed Sep. 30, 2020; See Patent Center.
All Office Actions; U.S. Appl. No. 17/037,776, filed Sep. 30, 2020; See Patent Center.
All Office Actions; U.S. Appl. No. 17/037,780, filed Sep. 30, 2020; See Patent Center.
All Office Actions; U.S. Appl. No. 17/037,789, filed Sep. 30, 2020; See Patent Center.
All Office Actions; U.S. Appl. No. 17/116,389, filed Dec. 9, 2020; See Patent Center.
All Office Actions; U.S. Appl. No. 17/704,023, filed Mar. 25, 2022; See Patent Center.
All Office Actions; U.S. Appl. No. 17/704,027, filed Mar. 25, 2022; See Patent Center.
All Office Actions; U.S. Appl. No. 17/704,028, filed Mar. 25, 2022; See Patent Center.
All Office Actions; U.S. Appl. No. 18/322,652, filed May 24, 2023. See Patent Center.
All Office Actions; U.S. Appl. No. 18/322,979, filed May 24, 2023. See Patent Center.
All Office Actions; U.S. Appl. No. 18/655,468, filed May 6, 2024; See Patent Center.
All Office Actions; U.S. Appl. No. 18/788,266, filed Jul. 30, 2024; See Patent Center.
Anbar, M. et al. "Organic Polymeric Polyphosphonates as Potential Preventive Agents of Dental Caries: In Vivo Experiments", J. Dent Res, vol. 53(5), 1974, pp. 1240-1244.
Barth Haas Isohop technical data sheet, Rev. 7, approved on Jul. 4, 2022, 3 pages.
Bhattacharya et al., "Inhibition of *Streptococcus mutans a*nd Other Oral Streptococci by Hop (*Humulus lupulus* L.) Constituents", Economic Botany, vol. 57, No. 1, Jan. 2003, pp. 118-125.
Bogdanova et al. "Antibiofilm activity of bioactive hop compounds humulone, lupulone and xanthohumol toward susceptible and resistant staphylococci", Research in Microbiology Journal, vol. 169, Issue 3, Apr. 2018, pp. 127-134.
Colgate, "What are the Signs and Symptoms of Gingivitis?", Online retrieved from ""https://www.colgate.com/en-us/oral-health/gum-disease/what-is-gingivitis-signs-and-symptoms" target="_blank"https://www.colgate.com/en-us/oral-health/gum-disease/what-is-gingivitis-signs-and-symptoms/a", Jul. 14, 2021, 8 Pages.
Comprehensive Separation and Structural Analyses of Polyphenolsand Related Compounds from Bracts of Hops, XP 55753130A1 Journal of Agricultural and food chemistry, Yoshihisa Tanaka, Year, 2014, pp. 2198-2206.
Database GNPD [Online] Mintel, anonymous: "Regular Mouth Wash", XP055753124, Retrieved from www.gnpd.com, Database accession No. 10441104 abstract, Feb. 5, 2009, pp. 1-3.
Database GNPD [Online] Mintel, anonymous: "Strawberry Milk Flavoured Anti-Cavity Toothpaste for Kids", XP055755176, Database accession No. 4757005; Apr. 18, 2017, p. 1-3.
Database GNPD [Online] Mintel, anonymous: "Whitening Tooth Powder", XP055755184, Database accession No. 1777364 abstract, Apr. 23, 2012, pp. 1-4.
Database GNPD [Online] Miintel, anonymous: "Daily Toothpaste!", XP055755179, Database accession No. 3287031 Abstract, Jul. 14, 2015, pp. 1-3.
Database WPI, Week 201807, Feb. 1, 2008 (Feb. 1, 2008), Thomson Scientific, London, GB; AN 2017-88895Q XP002801332, & CN 107485599 A (Univ Southwest) Dec. 19, 2017, pp. 4-8.
Gaffar, Abdul et al. "Effects of Editempa on Dental Calculus and Caries Formation in Vivo", Calcif Tissue Int 35,1983, pp. 362-365.
Harris, G., "Amino Acids and Peptides of Hops and Wort: I. Techniques and new compounds.", Journal of the Institute of Brewing, vol. 58, 1952, pp. 417-428.
Hopsteiner Store, XP 93067800A1, Consent to Cookies & Data processing, URL Link; https;//lwww.hopsteiner-shopde/en/about-hopsteiner, No Known Date, 3 pgs.
Hopsteiner, Beta Bio45%, XP55753265A1, No Known date, 3 Pages.
Jason Tetro, "The Secret to Better Teeth Found in Beer Breweries", Under the Microscope, Retrieved from the Internet: URL: https://www.popsci.com/blog-network/under-microscope/secret-better-teeth-found-beer-breweries/, Mar. 11, 2014, pp. 1-9.
Knowde, "Hopsteiner Beta Bio 45% Hops Extract-Anti-Microbial Agent", Online retrieved from "www.knowde.comstoreshopsteinerproducts", Feb. 16, 2021, 07 pages.
Mckenna Francine: "German Inventions in Everyday Use", XP055773018, Retrieved from the Internet: URL:https://www.germanpulse.com/2012/05/08/german-inventions-in-everyday-use/ [retrieved on Feb. 5, 2021] the whole document ; Jan. 1, 2012, 3 pages.
Meyer et al. "Quantifying Drug Combination Synergy along Potency and Efficacy Axes", Retrieved from Internet: https://pubmed.ncbi.nlm.nih.gov/30797775/, Feb. 27, 2019, 46 Pages.
Muhlemann, HR et al. "Reduction of Plaque and Gingivitis by Stannous Fluoride Stabilized with Amine Fluoride", Caries Research 15:2 , 1981,1 page.

(56) References Cited

OTHER PUBLICATIONS

Roger Stevens, "The Chemistry of Hop Constituents", Brewing Industry Research Foundation, Mar. 31, 1966, pp. 19-71.
Rotgans, J et al. "The Effect of Brushing with a Toothpaste Containing Amyloglucosidase and Glucose Oxidase on Dental Caries in Rats", Caries Res. 13, 1979, pp. 150-153.
Sharma, Siddharth et al. "Laboratory Evaluation of the Efficacy of Formulated Polyherbal Toothpaste "Oralis S" on Dental Caries in Rats", IJPRAS, vol. 3(2), 2014, pp. 47-50.
Simpson et al., "Factors Affecting Antibacterial Activity of Hop Compounds and Their Derivatives", Journal of Applied Bacteriology, vol. 72, 1992, pp. 327-334.
Spirit Dental, "A Step-by-Step Guide to Proper Teeth Brushing", Online retrieved from"https://spiritdental.com/blog/categories/dental-health/a-step-by-step-guide-to-proper-teeth-brushing", 2019; 02 pages.
Spiritdental.com_ A Step-by-Step Guide to Proper Teeth Brushing, "www.spiritdental.com", Published online Jul. 18, 2019, 5 Pages.
Stookey, G. K. et al. "Animal Caries Models For Evaluating Fluoride Dentifrices" Adv. Dent. Res 9(3), Nov. 1995, pp. 198-207.
Sullivan, RJ et al. "Development of an enhanced anticaries efficacy dual component dentifrice containing sodium fluoride and dicalcium phosphate dihydrate" Am J. Dent , 14 Spec No. 3A-11A, May 2001, pp. 1-2.
Wang et al., "Glycine inhibits the LPS-induced increase in cytosolic Ca2+ concentration and TNF α production in cardiomyocytes by activating a glycine receptor", Retrieved from: https://doi.org/10.1038/aps.2009.106, Jul. 20, 2009, pp. 1107-1114.
Xiang, et al., "Penetration and Bactericidal Efficacy of Two Oral Care Products in an Oral Biofilm Model", Am J Dent, vol. 31, Issue1, Feb. 2018, 07 pages.
Yang et al. "Relation between chemotaxis and consumption of amino acids in bacteria", Molecular Microbiology 96, 2015, pp. 1272-1282.
EPO Search Report and Opinion for 25199823.3 dated Jan. 22, 2026, 09 pages.

ORAL CARE COMPOSITIONS COMPRISING HOPS BETA ACIDS AND FLUORIDE IONS

FIELD OF THE INVENTION

The present invention is directed to compositions with improved anticaries activity. The present invention is also directed to compositions comprising hops beta acid, such as extract from *Humulus lupulus*, and fluoride.

BACKGROUND OF THE INVENTION

Oral care compositions, such as toothpaste and/or dentifrice compositions, can be applied to the oral cavity to clean and/or maintain the aesthetics and/or health of the teeth, gums, and/or tongue. Additionally, many oral care compositions are used to deliver active ingredients directly to oral care surfaces. For example, toothpaste compositions can have fluoride, such as sodium fluoride, sodium monofluorophosphate, and/or stannous fluoride, as an anticaries drug. While the effectiveness and safety of fluoride as an anticaries drug is well established, some consumers desire an oral care composition with lower amount (or a subtherapeutic amount) of fluoride ions.

However, current oral care compositions can either be fluoride-free, which do not provide enough, or any, protection from cavities, or have fluoride and provide anticavity protection. As such, there is a need for an oral care composition with a subtherapeutic amount of fluoride that still provides a therapeutic anticavity effect.

Additionally and/or alternatively, in many countries oral care compositions have a defined amount and/or concentration of fluoride ions since it is generally classified as an anticaries drug. Compositions with higher concentrations of fluoride ions can provide higher anticaries effect but can have safety concerns if unintentionally swallowed. These compositions must be prescribed and/or applied by a dental professional. As such, there is a need a for an oral care composition with a therapeutic amount of fluoride, but with a prescription strength effect.

SUMMARY OF THE INVENTION

Disclosed herein is an oral care composition comprising (a) hops extract comprising hops beta acid and hops oils, wherein the hops extract comprises from greater than 0% to less than 2.5%, by weight of the hops extract, of the hops oils, wherein the oral care composition comprises from about 0.01% to about 10%, by weight of the composition, of the hops beta acid, and wherein the hops beta acid comprises only non-hydrogenated hops beta acids; and (b) from about 0.01% to about 10%, by weight of the composition, of fluoride, where the oral care composition has a pH of greater than 7.

Also disclosed herein is an oral care composition comprising (a) from about 0.01% to about 10%, by weight of the composition, of hops beta acid; (b) from about 0.01% to about 10%, by weight of the composition, of stannous fluoride; and (c) citrate, where the oral care composition has a pH of greater than 7.

DETAILED DESCRIPTION OF THE INVENTION

The present invention is directed to oral care compositions that have fluoride, but provide an unexpectedly high anticavity benefit relative to the amount of fluoride present.

Dental caries, or tooth decay, is a breakdown of the teeth due to the acids made by bacteria. Cavities are caused by the acid produced by bacteria dissolving the hard tissues of the teeth, such as enamel, dentin, and/or cementum. The acid is produced by the bacteria when the bacteria breaks down food debris or sugar on the tooth's surface.

Fluoride works by making the tooth's surface less soluble to the acid produced by the bacteria, "plaque acid." Tooth's enamel is made from hydroxyapatite ($Ca_5(PO_4)_3(OH)$). Hydroxyapatite can be dissolved from the enamel at a pH of under 5.5 (demineralization). If hydroxyapatite is demineralized in the presence of fluoride ions, fluorapatite ($Ca_5(PO_4)_3(F)$) can remineralize on the surface of a tooth's enamel. In sum, this process is a replacement of a hydroxyl (OH) ion with a fluoride (F) ion. Fluorapatite is inherently less soluble than hydroxyapatite, even under acidic conditions. Thus, fluoride works as an anticaries drug to make the tooth's surface more resistant and less soluble to plaque acid.

While not wishing to being bound by theory, it is believed that the disclosed oral care compositions have an additional mechanism of action compared with fluoride ion therapy. In contrast to the single symptom treatment of fluoride (i.e. treating the result of plaque acid), the disclosed compositions are believed to have anticavity activity through a combination of mechanisms. While not wishing to being bound by theory, it is believed that the disclosed oral care compositions have an additional anticavity effect by providing one or more of the following outcomes: (1) suppressing plaque acid production, (2) neutralizing plaque acids that are produced, and/or (3) reducing the solubility of the hydroxyapatite hard tissue surface.

The suppression of plaque acid production can be accomplished by providing one or more antibacterial agents to kill the source of the plaque acid (i.e. the bacteria itself) and/or providing one or more biofilm modifiers to disrupt and embed antibacterial agents within the biofilm matrix.

Neutralizing the plaque acids can be accomplished by providing one or more biofilm modifiers to disrupt the biofilm matrix and/or providing one or more buffering agents to buffer the produced plaque acid and/or increasing the saturation of calcium ions on the enamel surface by providing one or more calcium ion sources.

Reducing the solubility of the hydroxyapatite hard tissue surface can be accomplished by providing one or more calcium ion sources. This can create a supersaturated environment of calcium and/or phosphate ions around the hydroxyapatite surface, which can shift the equilibrium of Formula 1 in favor of remineralization of hydroxyapatite according to Le Chatelier's principle.

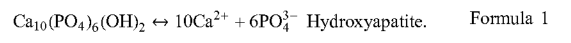

$$Ca_{10}(PO_4)_6(OH)_2 \leftrightarrow 10Ca^{2+} + 6PO_4^{3-} \text{ Hydroxyapatite.} \quad \text{Formula 1}$$

While each of these mechanisms might not be enough, on its own, to provide an anticavity benefit equivalent to a therapeutic dose of fluoride, in combination with each other and/or with fluoride these mechanisms can provide an improved and/or additional anticavity benefit. As such, the present invention is directed to oral care compositions that have fluoride, but provide an unexpectedly high anticavity benefit relative to the amount of fluoride present.

Definitions

To define more clearly the terms used herein, the following definitions are provided. Unless otherwise indicated, the following definitions are applicable to this disclosure. If a term is used in this disclosure but is not specifically defined herein, the definition from the IUPAC Compendium of Chemical Terminology, 2nd Ed (1997), can be applied, as long as that definition does not conflict with any other disclosure or definition applied herein, or render indefinite or non-enabled any claim to which that definition is applied.

The term "oral care composition", as used herein, includes a product, which in the ordinary course of usage, is not intentionally swallowed for purposes of systemic administration of particular therapeutic agents, but is rather retained in the oral cavity for a time sufficient to contact dental surfaces or oral tissues. Examples of oral care compositions include dentifrice, toothpaste, tooth gel, subgingival gel, mouth rinse, mousse, foam, mouth spray, lozenge, chewable tablet, chewing gum, tooth whitening strips, floss and floss coatings, breath freshening dissolvable strips, or denture care or adhesive product. The oral care composition may also be incorporated onto strips or films for direct application or attachment to oral surfaces.

"Active and other ingredients" useful herein may be categorized or described herein by their cosmetic and/or therapeutic benefit or their postulated mode of action or function. However, it is to be understood that the active and other ingredients useful herein can, in some instances, provide more than one cosmetic and/or therapeutic benefit or function or operate via more than one mode of action. Therefore, classifications herein are made for the sake of convenience and are not intended to limit an ingredient to the particularly stated function(s) or activities listed.

The term "orally acceptable carrier" comprises one or more compatible solid or liquid excipients or diluents which are suitable for topical oral administration. By "compatible," as used herein, is meant that the components of the composition are capable of being commingled without interaction in a manner which would substantially reduce the composition's stability and/or efficacy.

The term "substantially free" as used herein refers to the presence of no more than 0.05%, preferably no more than 0.01%, and more preferably no more than 0.001%, of an indicated material in a composition, by total weight of such composition.

The term "essentially free" as used herein means that the indicated material is not deliberately added to the composition, or preferably not present at analytically detectable levels. It is meant to include compositions whereby the indicated material is present only as an impurity of one of the other materials deliberately added.

While compositions and methods are described herein in terms of "comprising" various components or steps, the compositions and methods can also "consist essentially of" or "consist of" the various components or steps, unless stated otherwise.

As used herein, the word "or" when used as a connector of two or more elements is meant to include the elements individually and in combination; for example, X or Y, means X or Y or both.

As used herein, the articles "a" and "an" are understood to mean one or more of the material that is claimed or described, for example, "an oral care composition" or "a bleaching agent."

All measurements referred to herein are made at about 23° C. (i.e. room temperature) unless otherwise specified.

Generally, groups of elements are indicated using the numbering scheme indicated in the version of the periodic table of elements published in Chemical and Engineering News, 63 (5), 27, 1985. In some instances, a group of elements can be indicated using a common name assigned to the group; for example, alkali metals for Group 1 elements, alkaline earth metals for Group 2 elements, and so forth.

Several types of ranges are disclosed in the present invention. When a range of any type is disclosed or claimed, the intent is to disclose or claim individually each possible number that such a range could reasonably encompass, including end points of the range as well as any sub-ranges and combinations of sub-ranges encompassed therein.

The term "about" means that amounts, sizes, formulations, parameters, and other quantities and characteristics are not and need not be exact, but can be approximate and/or larger or smaller, as desired, reflecting tolerances, conversion factors, rounding off, measurement errors, and the like, and other factors known to those of skill in the art. In general, an amount, size, formulation, parameter or other quantity or characteristic is "about" or "approximate" whether or not expressly stated to be such. The term "about" also encompasses amounts that differ due to different equilibrium conditions for a composition resulting from a particular initial mixture. Whether or not modified by the term "about," the claims include equivalents to the quantities. The term "about" can mean within 10% of the reported numerical value, preferably within 5% of the reported numerical value.

The oral care composition can be in any suitable form, such as a solid, liquid, powder, paste, or combinations thereof. The oral care composition can be dentifrice, tooth gel, subgingival gel, mouth rinse, mousse, foam, mouth spray, lozenge, chewable tablet, chewing gum, tooth whitening strips, floss and floss coatings, breath freshening dissolvable strips, or denture care or adhesive product. The components of the dentifrice composition can be incorporated into a film, a strip, a foam, or a fiber-based dentifrice composition. The oral care composition can include a variety of active and inactive ingredients, such as, for example, but not limited to a hops extract, a tin ion source, a calcium ion source, water, a fluoride ion source, zinc ion source, one or more polyphosphates, humectants, surfactants, other ingredients, and the like, as well as any combination thereof, as described below.

Section headers are provided below for organization and convenience only. The section headers do not suggest that a compound cannot be within more than one section. In fact, compounds can fall within more than one section. For example, stannous chloride can be both a tin ion source and a biofilm modifier, stannous fluoride can be both a tin ion source and a fluoride ion source, glycine can be an amino acid, a buffering agent, and/or a biofilm modifier, among numerous other compounds that can fit amongst several categories and/or sections.

*Humulus lupulus*

The oral care compositions of the present invention comprise at least one hops compound from Formula I and/or Formula IV. The compound from Formula I and/or Formula IV can be provided by any suitable source, such as an extract from *Humulus lupulus* or Hops, *Humulus lupulus* itself, a synethically derived compound, and/or salts, prodrugs, or other analogs thereof. The hops extract can comprise one or more hops alpha acids, one or more hops iso-alpha acids, one or more hops beta acids, one or more hops oils, one or more flavonoids, one or more solvents, and/or water. Suitable hops alpha acids (generically shown in Formula I) can include humulone (Formula II), adhumulone, cohumulone, posthumulone, prehumulone, and/or mixtures thereof. Suitable hops iso-alpha acids can include cis-isohumulone and/or trans-isohumulone. The isomerization of humulone into trans-isohumulone can be represented by Formula III.

Formula I

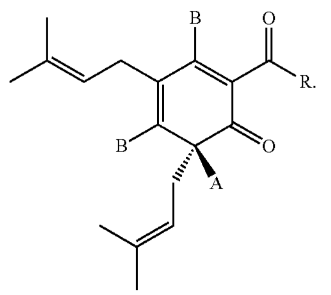

Hops Alpha Acids

A is the acidic hydroxyl functional group in the alpha position, B are the acidic hydroxyl functional groups in the beta position, and R is an alkyl functional group.

Formula II

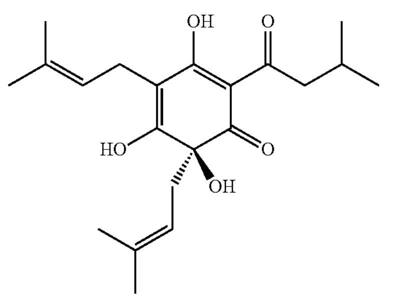

Humulone

Formula III

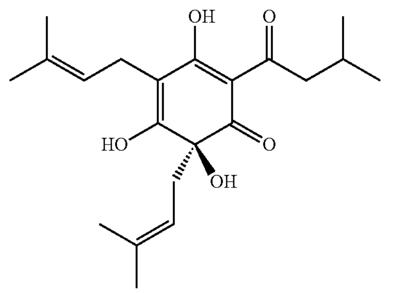

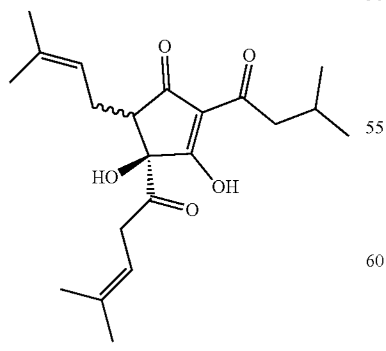

Isomerization of
Humulone to isohumulone.

Suitable hops beta acids can include lupulone, adlupulone, colupulone, and/or mixtures thereof. A suitable hops beta acid can include a compound a described in Formula IV, V, VI, and/or VII.

Formula IV

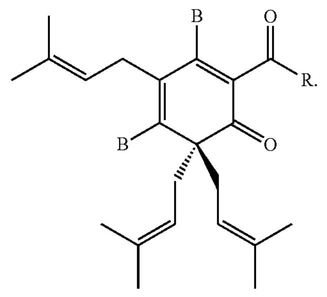

Hops Beta Acids

B are the acidic hydroxyl functional groups in the beta position and R is an alkyl functional group.

Formula V

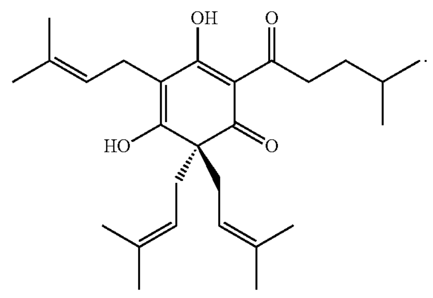

Lupulone

Formula VI

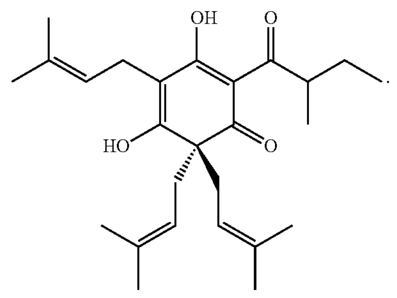

Adlupulone

Formula VII

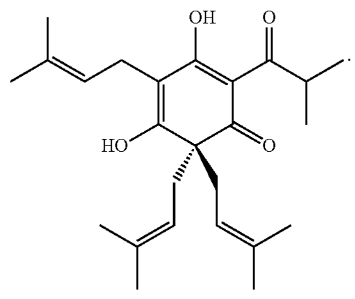

Colupulone

While hops alpha acids can demonstrate some antibacterial activity, hops alpha acids also have a bitter taste. The bitterness provided by hops alpha acids can be suitable for beer, but are not suitable for use in oral care compositions. In contrast, hops beta acids can be associated with a higher antibacterial and/or anticaries activity, but not as bitter a taste. Thus, a hops extract with a higher proportion of beta acids to alpha acids than normally found in nature, can be suitable for use in oral care compositions for use as an antibacterial and/or anticaries agent.

A natural hops source can comprise from about 2% to about 12%, by weight of the hops source, of hops beta acids depending on the variety of hops. Hops extracts used in other contexts, such as in the brewing of beer, can comprise from about 15% to about 35%, by weight of the extract, of hops beta acids. The hops extract desired herein can comprise at least about 35%, at least about 40%, at least about 45%, from about 35% to about 95%, from about 40% to about 90%, or from about 45% to about 99%, of hops beta acids. The hops beta acids can be in an acidic form (i.e. with attached hydrogen atom(s) to the hydroxyl functional group (s)) or as a salt form.

A suitable hops extract is described in detail in U.S. Pat. No. 7,910,140, which is herein incorporated by reference in its entirety. The hops beta acids desired can be non-hydrogenated, partially hydrogenated by a non-naturally occurring chemical reaction, or hydrogenated by a non-naturally occurring chemical reaction. The hops beta acid can be essentially free of or substantially free of hydrogenated hops beta acid and/or hops acid. A non-naturally occurring chemical reaction is a chemical reaction that was conducted with the aid of chemical compound not found within *Humulus lupulus*, such as a chemical hydrogenation reaction conducted with high heat not normally experienced by *Humulus lupulus* in the wild and/or a metal catalyst.

A natural hops source can comprise from about 2% to about 12%, by weight of the hops source, of hops alpha acids. Hops extracts used in other contexts, such as in the brewing of beer, can comprise from about 15% to about 35%, by weight of the extract, of hops alpha acids. The hops extract desired herein can comprise less than about 10%, less than about 5%, less than about 1%, or less than about 0.5%, by weight of the extract, of hops alpha acids.

Hops oils can include terpene hydrocarbons, such as myrcene, humulene, caryophyllene, and/or mixtures thereof. The hops extract desired herein can comprise less than 5%, less than 2.5%, or less than 2%, by weight of the extract, of one or more hops oils.

Flavonoids present in the hops extract can include xanthohumol, 8-prenylnaringenin, isoxanthohumol, and/or mixtures thereof. The hops extract can be substantially free of, essentially free of, free of, or have less than 250 ppm, less than 150 ppm, and/or less than 100 ppm of one or more flavonoids.

As described in U.S. Pat. No. 5,370,863, hops acids have been previously added to oral care compositions. However, the oral care compositions taught by U.S. Pat. No. 5,370,863 only included up to 0.01%, by weight of the oral care composition. While not wishing to be bound by theory, it is believed that U.S. Pat. No. 5,370,863 could only incorporate a low amount of hops acids because of the bitterness of hops alpha acids. A hops extract with a low level of hops alpha acids would not have this concern.

The hops compound can be combined with or free from an extract from another plant, such as a species from genus *Magnolia*. The hops compounds can be combined with or free from triclosan.

The oral care composition can comprise from about 0.01% to about 10%, greater than 0.01% to about 10%, from about 0.05%, to about 10%, from about 0.1% to about 10%, from about 0.2% to about 10%, from about 0.2% to about 10%, from about 0.2% to about 5%, from about 0.25% to about 2%, from about 0.05% to about 2%, or from greater than 0.25% to about 2%, of hops beta acid, as described herein. The hops beta acids can be provided by a suitable hops extract, the hops plant itself, or a synthetically derived compound. The hops beta acid can be provided as neutral, acidic compounds, and/or as salts with a suitable counter ion, such as sodium, potassium, ammonia, or any other suitable counter ion.

The hops beta acid can be provided by a hops extract, such as an extract from *Humulus lupulus* with at least 35%, by weight of the extract, of hops beta acid and less than 1%, by weight of the hops extract, of hops alpha acid. The oral care composition can comprise 0.01% to about 10%, greater than 0.01% to about 10%, from about 0.05%, to about 10%, from about 0.1% to about 10%, from about 0.2% to about 10%, from about 0.2% to about 10%, from about 0.2% to about 5%, from about 0.25% to about 2%, from about 0.05% to about 2%, or from greater than 0.25% to about 2%, of hops extract, as described herein.

Fluoride Ion Source

The oral care composition comprises fluoride, such as from a fluoride ion source. The fluoride ion source can comprise one or more fluoride containing compounds, such as stannous fluoride, sodium fluoride, titanium fluoride, calcium fluoride, calcium phosphate silicate fluoride, potassium fluoride, amine fluoride, sodium monofluorophosphate, zinc fluoride, and/or mixtures thereof.

The fluoride ion source and the tin ion source can be the same compound, such as for example, stannous fluoride, which can generate tin ions and fluoride ions. Additionally, the fluoride ion source and the tin ion source can be separate compounds, such as when the tin ion source is stannous chloride and the fluoride ion source is sodium monofluorophosphate or sodium fluoride.

The fluoride ion source and the zinc ion source can be the same compound, such as for example, zinc fluoride, which can generate zinc ions and fluoride ions. Additionally, the fluoride ion source and the zinc ion source can be separate compounds, such as when the zinc ion source is zinc phosphate and the fluoride ion source is stannous fluoride.

The fluoride ion source can be substantially free of, essentially free of, or free of stannous fluoride. Thus, the oral care composition can comprise sodium fluoride, potassium fluoride, amine fluoride, sodium monofluorophosphate, zinc fluoride, and/or mixtures thereof.

The oral care composition can comprise a fluoride ion source capable of providing from about 50 ppm to about 5000 ppm, and preferably from about 500 ppm to about 3000 ppm of free fluoride ions. To deliver the desired amount of fluoride ions, the fluoride ion source may be present in the oral care composition at an amount of from about 0.0025% to about 5%, from about 0.01% to about 10%, from about 0.2% to about 1%, from about 0.5% to about 1.5%, or from about 0.3% to about 0.6%, by weight of the oral care composition.

Tin Ion Source

The oral care composition of the present invention can comprise tin, such as from a tin ion source. The tin ion source can be any suitable compound that can provide tin ions in an oral care composition and/or deliver tin ions to the oral cavity when the dentifrice composition is applied to the oral cavity. The tin ion source can comprise one or more tin containing compounds, such as stannous fluoride, stannous chloride, stannous bromide, stannous iodide, stannous oxide, stannous oxalate, stannous sulfate, stannous sulfide, stannic fluoride, stannic chloride, stannic bromide, stannic iodide, stannic sulfide, and/or mixtures thereof. Tin ion source can comprise stannous fluoride, stannous chloride, and/or mixture thereof. The tin ion source can also be a fluoride-free tin ion source, such as stannous chloride.

The oral care composition can comprise from about 0.0025% to about 5%, from about 0.01% to about 10%, from about 0.2% to about 1%, from about 0.5% to about 1.5%, or from about 0.3% to about 0.6%, by weight of the oral care composition, of tin ion source.

Calcium Ion Source

The oral care composition of the present invention can comprise calcium, such as from a calcium ion source. The calcium ion source can be any suitable compound or molecule that can provide calcium ions in an oral care composition and/or deliver calcium ions to the oral cavity when the oral care composition is applied to the oral cavity. The calcium ion source can comprise a calcium salt, a calcium abrasive, and/or combinations thereof. In some cases, a calcium salt may also be considered a calcium abrasive or a calcium abrasive may also be considered a calcium salt.

The calcium ion source can comprise a calcium abrasive. The calcium abrasive can be any suitable abrasive compound that can provide calcium ions in an oral care composition and/or deliver calcium ions to the oral cavity when the oral care composition is applied to the oral cavity. The calcium abrasive can comprise one or more calcium abrasive compounds, such as calcium carbonate, precipitated calcium carbonate (PCC), ground calcium carbonate (GCC), chalk, dicalcium phosphate, calcium pyrophosphate, and/or mixtures thereof.

The calcium ion source can comprise a calcium salt, or a compound that can provide calcium ions in an oral care composition and/or deliver calcium ions to the oral cavity when the oral care composition is applied to the oral cavity that can not act as an abrasive. The calcium salt can comprise one or more calcium compounds, such as calcium chloride, calcium nitrate, calcium phosphate, calcium lactate, calcium oxalate, calcium oxide, calcium gluconate, calcium citrate, calcium bromide, calcium iodate, calcium iodide, hydroxyapatite, fluorapatite, calcium sulfate, calcium glycerophosphate, and/or combinations thereof.

The oral care composition can comprise from about 5% to about 70%, from about 10% to about 50%, from about 10% to about 60%, from about 20% to about 50%, from about 25% to about 40%, or from about 1% to about 50% of a calcium ion source.

Buffering Agent

The oral care composition can comprise a buffering agent. The buffering agent can be a weak acid or base that can maintain a particular pH at a selected site in the oral cavity. For example, the buffering agent can maintain a pH at a tooth's surface to mitigate the impact of plaque acids produced by bacteria. The buffering agent can comprise a conjugate acid of an ion also present in the oral care composition. For example, if the calcium ion source comprises calcium carbonate, the buffering agent can comprise a bicarbonate anion ($—HCO_3$-). The buffering agent can comprise a conjugate acid/base pair, such as citric acid and sodium citrate.

Suitable buffering systems can include phosphate, citrate salts, carbonate/bicarbonate salts, a tris buffer, imidazole, urea, borate, and/or combinations thereof. Suitable buffering agents include bicarbonate salts, such as sodium bicarbonate, glycine, orthophosphate, arginine, urea, and or/combinations thereof.

The oral care composition can comprise from about 1% to about 30%, from about 5% to about 25% or from about 10% to about 20%, of one or more buffering agents.

Biofilm Modifier

The oral care composition can comprise one or more biofilm modifiers. A biofilm modifier can comprise a polyol, an ammonia generating compound, and/or a glucosyltransferase inhibitor.

A polyol is an organic compound with more than one hydroxyl functional groups. The polyol can be any suitable compound that can weakly associate, interact, or bond to tin ions while the oral care composition is stored prior to use. The polyol can be a sugar alcohol, which area class of polyols that can be obtained through the hydrogenation of sugar compounds with the formula $(CHOH)_nH_2$. The polyol can be glycerin, erythritol, xylitol, sorbitol, mannitol, butylene glycol, lactitol, and/or combinations thereof. The oral care composition can comprise 0.01% to about 70%, from about 5% to about 70%, from about 5% to about 50%, from about 10% to about 60%, from about 10% to about 25%, or from about 20% to about 80%, by weight of the oral care composition, of a polyol.

The ammonia generating compound can be any suitable compound that can generate ammonia upon delivery to the oral cavity. Suitable ammonia generating compounds include arginine, urea, and/or combinations thereof. The oral care composition can comprise from about 0.01% to about 10%, from about 1% to about 5%, or from about 1% to about 25% of one or more ammonia generating compounds.

The glucosyltransferase inhibitor can be any suitable compound that can inhibit a glucosyltransferase. Glucosyltransferases are enzymes that can establish natural glycosidic linkages. In particular, these enzymes break down poly- or oligosaccharide moieties into simple sugars for bacteria associated with dental caries. As such, any compound that can inhibit this process can help prevent dental caries. Suitable glucosyltransferase inhibitors include oleic acid, epicatechin, tannins, tannic acid, moenomycin, caspofungin, ethambutol, lufenuron, and/or combinations thereof. The oral care composition can comprise from about 0.001% to about 5%, from about 0.01% to about 2%, or about 1% of one or more glucosyltransferase inhibitors.

Metal Ion Source

The oral care composition can comprise metal, such as from a metal ion source comprising one or more metal ions. The metal ion source can comprise or be in addition to the tin ion source and/or the zinc ion source, as described herein. Suitable metal ion sources include compounds with metal ions, such as, but not limited to Sn, Zn, Cu, Mn, Mg, Sr, Ti, Fe, Mo, B, Ba, Ce, Al, In and/or mixtures thereof. The trace metal source can be any compound with a suitable metal and any accompanying ligands and/or anions.

Suitable ligands and/or anions that can be paired with metal ion sources include, but are not limited to acetate, ammonium sulfate, benzoate, bromide, borate, carbonate, chloride, citrate, gluconate, glycerophosphate, hydroxide, iodide, oxide, propionate, D-lactate, DL-lactate, orthophosphate, pyrophosphate, sulfate, nitrate, tartrate, and/or mixtures thereof.

The oral care composition can comprise from about 0.01% to about 10%, from about 1% to about 5%, or from about 0.5% to about 15% of a metal ion source.

Antibacterial Agents

The oral care composition can comprise one or more antibacterial agents. Suitable antibacterial agents include any molecule that provides antibacterial activity in the oral cavity. Suitable antibacterial agents include hops acids, tin ion sources, benzyl alcohol, sodium benzoate, menthylglycyl acetate, menthyl lactate, L-menthol, o-neomenthol, chlorophyllin copper complex, phenol, oxyquinoline, and/or combinations thereof.

The oral care composition can comprise from about 0.01% to about 10%, from about 1% to about 5%, or from about 0.5% to about 15% of an antibacterial agent.

Bioactive Materials

The oral care composition can also include bioactive materials suitable for the remineralization of a tooth. Suitable bioactive materials include bioactive glasses, Novamin™, Recaldent™, hydroxyapatite, one or more amino acids, such as, for example, arginine, citrulline, glycine, lysine, or histidine, or combinations thereof. Suitable examples of compositions comprising arginine are found in U.S. Pat. Nos. 4,154,813 and 5,762,911, which are herein incorporated by reference in their entirety. Other suitable bioactive materials include any calcium phosphate compound. Other suitable bioactive materials include compounds comprising a calcium source and a phosphate source.

Amino acids are organic compounds that contain an amine functional group, a carboxyl functional group, and a side chain specific to each amino acid. Suitable amino acids include, for example, amino acids with a positive or negative side chain, amino acids with an acidic or basic side chain, amino acids with polar uncharged side chains, amino acids with hydrophobic side chains, and/or combinations thereof. Suitable amino acids also include, for example, arginine, histidine, lysine, aspartic acid, glutamic acid, serine, threonine, asparagine, glutamine, cysteine, selenocysteine, glycine, proline, alanine, valine, isoleucine, leucine, methionine, phenylalanine, tyrosine, tryptophan, citrulline, ornithine, creatine, diaminobutonic acid, diaminoproprionic acid, salts thereof, and/or combinations thereof.

Bioactive glasses are comprising calcium and/or phosphate which can be present in a proportion that is similar to hydroxyapatite. These glasses can bond to the tissue and are biocompatible. Bioactive glasses can include a phosphopeptide, a calcium source, phosphate source, a silica source, a sodium source, and/or combinations thereof.

The oral care composition can comprise from about 0.01% to about 20%, from about 0.1% to about 10%, or from about 1% to about 10% of a bioactive material by weight of the oral care composition.

Abrasive

The oral care composition can comprise a calcium abrasive, as described herein, and/or a non-calcium abrasive, such as bentonite, silica gel (by itself, and of any structure), precipitated silica, amorphous precipitated silica (by itself, and of any structure as well), hydrated silica, perlite, titanium dioxide, calcium pyrophosphate, dicalcium phosphate dihydrate, alumina, hydrated alumina, calcined alumina, aluminum silicate, insoluble sodium metaphosphate, insoluble potassium metaphosphate, insoluble magnesium carbonate, zirconium silicate, particulate thermosetting resins and other suitable abrasive materials. Such materials can be introduced into the oral care compositions to tailor the polishing characteristics of the target dentifrice formulation. The oral care composition can comprise from about 5% to about 70%, from about 10% to about 50%, from about 10% to about 60%, from about 20% to about 50%, from about 25% to about 40%, or from about 1% to about 50%, by weight of the oral care composition, of the non-calcium abrasive.

Alternatively, the oral care composition can be substantially free of, essentially free of, or free of silica, alumina, or any other non-calcium abrasive. The oral care composition can comprise less than about 5%, less than about 1%, less than about 0.5%, less than about 0.1%, or 0% of a non-calcium abrasive, such as silica and/or alumina.

Water

The oral care composition of the present invention can be anhydrous, a low water formulation, or a high water formulation. In total, the oral care composition can comprise from 0% to about 99%, from about 5% to about 75%, about 20% or greater, about 30% or greater, or about 50% or greater by weight of the composition, of water. Preferably, the water is USP water.

In a high water oral care composition and/or toothpaste formulation, the oral care composition comprises from about 45% to about 75%, by weight of the composition, of water. The high water oral care composition and/or toothpaste formulation can comprise from about 45% to about 65%, from about 45% to about 55%, or from about 46% to about 54%, by weight of the composition, of water. The water may be added to the high water formulation and/or may come into the composition from the inclusion of other ingredients.

In a low water oral care composition and/or toothpaste formulation, the oral care composition comprises from about 5% to about 45%, by weight of the composition, of water. The low water oral care composition can comprise from about 5% to about 35%, from about 10% to about 25%, or from about 20% to about 25%, by weight of the composition, of water. The water may be added to the low water formulation and/or may come into the composition from the inclusion of other ingredients.

In an anhydrous oral care composition and/or toothpaste formulation, the oral care composition comprises less than about 10%, by weight of the composition, of water. The anhydrous composition comprises less than about 5%, less than about 1%, or 0%, by weight of the composition, of water. The water may be added to the anhydrous formulation and/or may come into the composition from the inclusion of other ingredients.

A mouth rinse formulation comprises from about 75% to about 99%, from about 75% to about 95%, or from about 80% to about 95% of water.

The composition can also comprise other orally acceptable carrier materials, such as alcohol, humectants, polymers, surfactants, and acceptance improving agents, such as flavoring, sweetening, coloring and/or cooling agents.

pH

The pH of the disclosed composition can be from about 4 to about 10, from about 7 to about 10, greater than 7 to about 10, greater than 8 to about 10, greater than 7, greater than 7.5, greater than 8, greater than 9, or from about 8.5 to about 10.

Zinc Ion Source

The oral care composition can comprise zinc, such as from a zinc ion source. The zinc ion source can comprise one or more zinc containing compounds, such as zinc fluoride, zinc lactate, zinc oxide, zinc phosphate, zinc chloride, zinc acetate, zinc hexafluorozirconate, zinc sulfate, zinc tartrate, zinc gluconate, zinc citrate, zinc malate, zinc glycinate, zinc pyrophosphate, zinc metaphosphate, zinc oxalate, and/or zinc carbonate. The zinc ion source can be a fluoride-free zinc ion source, such as zinc phosphate, zinc oxide, and/or zinc citrate.

The zinc ion source may be present in the total oral care composition at an amount of from about 0.01% to about 10%, from about 0.2% to about 1%, from about 0.5% to about 1.5%, or from about 0.3% to about 0.6%, by weight of the dentifrice composition.

Polyphosphates

The oral care composition can comprise polyphosphate, such as from a polyphosphate source. A polyphosphate source can comprise one or more polyphosphate molecules. Polyphosphates are a class of materials obtained by the dehydration and condensation of orthophosphate to yield linear and cyclic polyphosphates of varying chain lengths. Thus, polyphosphate molecules are generally identified with an average number (n) of polyphosphate molecules, as described below. A polyphosphate is generally understood to consist of two or more phosphate molecules arranged primarily in a linear configuration, although some cyclic derivatives may be present.

Preferred polyphosphates are those having an average of two or more phosphate groups so that surface adsorption at effective concentrations produces sufficient non-bound phosphate functions, which enhance the anionic surface charge as well as hydrophilic character of the surfaces. Preferred in this invention are the linear polyphosphates having the formula: $XO(XPO_3)_nX$, wherein X is sodium, potassium, ammonium, or any other alkali metal cations and n averages from about 2 to about 21. Alkali earth metal cations, such as calcium, are not preferred because they tend to form insoluble fluoride salts from aqueous solutions comprising a fluoride ions and alkali earth metal cations. Thus, the oral care compositions disclosed herein can be free of, essentially free of, or substantially free of calcium pyrophosphate.

Some examples of suitable polyphosphate molecules include, for example, pyrophosphate (n=2), tripolyphosphate (n=3), tetrapolyphosphate (n=4), sodaphos polyphosphate (n=6), hexaphos polyphosphate (n=13), benephos polyphosphate (n=14), hexametaphosphate (n=21), which is also known as Glass H. Polyphosphates can include those polyphosphate compounds manufactured by FMC Corporation, ICL Performance Products, and/or Astaris.

The oral care composition can comprise from about 0.01% to about 15%, from about 0.1% to about 10%, from about 0.5% to about 5%, from about 1 to about 20%, or about 10% or less, by weight of the oral care composition, of the polyphosphate source.

Humectants

The oral care composition can comprise one or more humectants, have low levels of a humectant, be substantially free of, essentially free of, or be free of a humectant. Humectants serve to add body or "mouth texture" to an oral care composition or dentifrice as well as preventing the dentifrice from drying out. Suitable humectants include polyethylene glycol (at a variety of different molecular weights), propylene glycol, glycerin (glycerol), erythritol, xylitol, sorbitol, mannitol, butylene glycol, lactitol, hydrogenated starch hydrolysates, and/or mixtures thereof. The oral care composition can comprise one or more humectants each at a level of from 0 to about 70%, from about 5% to about 50%, from about 10% to about 60%, or from about 20% to about 80%, by weight of the oral care composition.

Surfactants

The oral care composition can comprise one or more surfactants. The surfactants can be used to make the compositions more cosmetically acceptable. The surfactant is preferably a detersive material which imparts to the composition detersive and foaming properties. Suitable surfactants are safe and effective amounts of anionic, cationic, nonionic, zwitterionic, amphoteric and betaine surfactants.

Suitable anionic surfactants include, for example, the water soluble salts of alkyl sulfates having from 8 to 20 carbon atoms in the alkyl radical and the water-soluble salts of sulfonated monoglycerides of fatty acids having from 8 to 20 carbon atoms. Sodium lauryl sulfate (SLS) and sodium coconut monoglyceride sulfonates are examples of anionic surfactants of this type. Other suitable anionic surfactants include sarcosinates, such as sodium lauroyl sarcosinate, taurates, sodium lauryl sulfoacetate, sodium lauroyl isethionate, sodium laureth carboxylate, and sodium dodecyl benzene sulfonate. Combinations of anionic surfactants can also be employed.

Another suitable class of anionic surfactants are alkyl phosphates. The surface active organophosphate agents can have a strong affinity for enamel surface and have sufficient surface binding propensity to desorb pellicle proteins and remain affixed to enamel surfaces. Suitable examples of organophosphate compounds include mono-, di- or triesters represented by the general structure below wherein $Z_1$, $Z_2$, or $Z_3$ may be identical or different with at least one being an organic moiety. $Z_1$, $Z_2$, or $Z_3$ can be selected from linear or branched, alkyl or alkenyl group of from 1 to 22 carbon atoms, optionally substituted by one or more phosphate groups; alkoxylated alkyl or alkenyl, (poly) saccharide, polyol or polyether group.

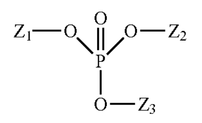

Some other agents include alkyl or alkenyl phosphate esters represented by the following structure:

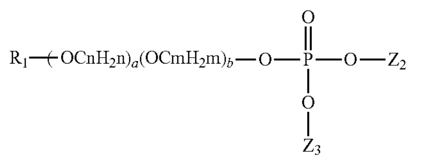

wherein $R_1$ represents a linear or branched, alkyl or alkenyl group of from 6 to 22 carbon atoms, optionally substituted by one or more phosphate groups; n and m, are individually and separately, 2 to 4, and a and b, individually and separately, are 0 to 20; Z and Z may be identical or different, each represents hydrogen, alkali metal, ammonium, protonated alkyl amine or protonated functional alkylamine, such as analkanolamine, or a R—(OCH2)(OCH)— group. Examples of suitable agents include alkyl and alkyl (poly) alkoxy phosphates such as lauryl phosphate; PPGS ceteareth-10 phosphate; laureth-1 phosphate; laureth-3 phosphate; laureth-9 phosphate; trilaureth-4 phosphate; $C_{12-18}$ PEG 9 phosphate; and sodium dilaureth-10 phosphate. The alkyl phosphate can be polymeric. Examples of polymeric alkyl phosphates include those containing repeating alkoxy groups as the polymeric portion, in particular 3 or more ethoxy, propoxy isopropoxy or butoxy groups.

Other suitable anionic surfactants are sarcosinates, isethionates and taurates, especially their alkali metal or ammonium salts. Examples include: lauroyl sarcosinate, myristoyl sarcosinate, palmitoyl sarcosinate, stearoyl sarcosinate oleoyl sarcosinate, or combinations thereof.

Other suitable anionic surfactants include sodium or potassium alkyl sulfates, such as sodium lauryl sulfate, acyl isethionates, acyl methyl isethionates, alkyl ether carboxylates, acyl alaninates, acyl gulatames, acyl glycinates, acyl sarconsinates, sodium methyl acyl taurates, sodium laureth sulfosuccinates, alpha olefin sulfonates, alkyl benze sulfonates, sodium lauroyl lactylate, sodium laurylglucosides hydroxypropyl sulfonate, and/or combinations.

Zwitterionic or amphoteric surfactants useful herein include derivatives of aliphatic quaternary ammonium, phosphonium, and Sulfonium compounds, in which the aliphatic radicals can be straight chain or branched, and one of the aliphatic substituents contains from 8 to 18 carbon atoms and one contains an anionic water-solubilizing group, e.g., carboxy, sulfonate, sulfate, phosphate or phosphonate. Suitable betaine surfactants are disclosed in U.S. Pat. No. 5,180,577. Typical alkyl dimethyl betaines include decyl betaine or 2-(N-decyl-N,N-dimethylammonio) acetate, coco-betaine or 2-(N-coco-N,N-dimethyl ammonio)acetate, myristyl betaine, palmityl betaine, lauryl betaine, cetyl betaine, cetyl betaine, stearyl betaine, etc. The amidobetaines can be exemplified by cocoamidoethyl betaine, cocoamidopropyl betaine (CADB), and lauramidopropyl betaine. Other suitable amphoteric surfactants include betaines, sultaines, sodium laurylamphoacetates, alkylamphodiacetates, and/or combinations thereof.

Cationic surfactants useful in the present invention include, for example, derivatives of quaternary ammonium compounds having one long alkyl chain containing from 8 to 18 carbon atoms such as lauryl trimethylammonium chloride; cetyl pyridinium chloride; cetyl trimethylammonium bromide; cetyl pyridinium fluoride or combinations thereof.

Nonionic surfactants that can be used in the compositions of the present invention include, for example, compounds produced by the condensation of alkylene oxide groups (hydrophilic in nature) with an organic hydrophobic compound which may be aliphatic or alkylaromatic in nature. Examples of suitable nonionic surfactants can include the Pluronics® which are poloxamers, polyethylene oxide condensates of alkyl phenols, products derived from the condensation of ethylene oxide with the reaction product of propylene oxide and ethylene diamine, ethylene oxide condensates of aliphatic alcohols, long chain tertiary amine oxides, long chain tertiary phosphine oxides, long chain dialkyl sulfoxides and combinations of such materials. Other suitable non-ionic surfactants includes alkyl glucamides, alkyl glucosides, and/or combinations thereof.

The one or more surfactants can also include one or more natural and/or naturally derived surfactants. Natural surfactants can include surfactants that are derived from natural products and/or surfactants that are minimally or not processed. Natural surfactants can include hydrogenated, non-hydrogenated, or partially hydrogenated vegetable oils, olus oil, *Passiflora incarnata* oil, *Candelilla cera, coco*-caprylate, caprate, dicaprylyl ether, lauryl alcohol, myristyl myristate, dicaprylyl ether, caprylic acid, caprylic ester, octyl decanoate, octyl octanoate, undecane, tridecane, decyl oleate, oleic acid decylester, cetyl palmitate, stearic acid, palmitic acid, glyceryl stearate, hydrogenated, non-hydrogenated, or partially hydrogenated vegetable glycerides, Polyglyceryl-2 dipolyhydroxystearate, cetearyl alcohol, sucrose polystearate, glycerin, octadodecanol, hydrolyzed, partially hydrolyzed, or non-hydrolyzed vegetable protein, hydrolyzed, partially hydrolyzed, or non-hydrolyzed wheat protein hydrolysate, polyglyceryl-3 diisostearate, glyceryl oleate, myristyl alcohol, cetyl alcohol, sodium cetearyl sulfate, cetearyl alcohol, glyceryl laurate, capric triglyceride, coco-glycerides, lectithin, dicaprylyl ether, xanthan gum, sodium coco-sulfate, ammonium lauryl sulfate, sodium cocoyl sulfate, sodium cocoyl glutamate, polyalkylglucosides, such as decyl glucoside, cetearyl glucoside, cetyl stearyl polyglucoside, coco-glucoside, and lauryl glucoside, and/or combinations thereof. Natural surfactants can include any of the Natrue ingredients marketed by BASF, such as, for example, CegeSoft®, Cetiol®, Cutina®, Dehymuls®, Emulgade®, Emulgin®, Eutanol®, Gluadin®, Lameform®, LameSoft®, Lanette®, Monomuls®, Myritol®, Plantacare®, Plantaquat®, Platasil®, Rheocare®, Sulfopon®, Texapon®, and/or combinations thereof.

Other specific examples of surfactants include sodium lauryl sulfate, sodium lauryl isethionate, sodium lauroyl methyl isethionate, sodium cocoyl glutamate, sodium dodecyl benzene sulfonate, alkali metal or ammonium salts of lauroyl sarcosinate, myristoyl sarcosinate, palmitoyl sarcosinate, stearoyl sarcosinate and oleoyl sarcosinate, polyoxyethylene sorbitan monostearate, isostearate and laurate, sodium lauryl sulfoacetate, N-lauroyl sarcosine, the sodium, potassium, and ethanolamine salts of N-lauroyl, N-myristoyl, or N-palmitoyl sarcosine, polyethylene oxide condensates of alkyl phenols, cocoamidopropyl betaine, lauramidopropyl betaine, palmityl betaine, sodium cocoyl glutamate, and the like. Additional surfactants desired include fatty acid salts of glutamate, alkyl glucoside, salts of taurates, betaines, caprylates, and/or mixtures thereof. The oral care composition can also be sulfate free.

The oral care composition can comprise one or more surfactants each at a level from about 0.01% to about 15%, from about 0.3% to about 10%, or from about 0.3% to about 2.5%, by weight of the oral care composition.

Thickening Agents

The oral care composition can comprise one or more thickening agents. Thickening agents can be useful in the oral care compositions to provide a gelatinous structure that stabilizes the dentifrice and/or toothpaste against phase separation. Suitable thickening agents include polysaccharides, polymers, and/or silica thickeners.

The thickening agent can comprise one or more polysaccharides. Some non-limiting examples of polysaccharides include starch; glycerite of starch; gums such as gum karaya (sterculia gum), gum tragacanth, gum arabic, gum ghatti, gum acacia, xanthan gum, guar gum and cellulose gum; magnesium aluminum silicate (Veegum); carrageenan; sodium alginate; agar-agar; pectin; gelatin; cellulose compounds such as cellulose, microcrystalline cellulose, carboxymethyl cellulose, hydroxyethyl cellulose, hydroxypropyl cellulose, hydroxymethyl cellulose, hydroxymethyl carboxypropyl cellulose, methyl cellulose, ethyl cellulose, and sulfated cellulose; natural and synthetic clays such as hectorite clays; and mixtures thereof.

Other polysaccharides that are suitable for use herein include carageenans, gellan gum, locust bean gum, xanthan gum, carbomers, poloxamers, modified cellulose, and mixtures thereof. Carageenan is a polysaccharide derived from seaweed. There are several types of carageenan that may be distinguished by their seaweed source and/or by their degree of and position of sulfation. The thickening agent can comprise kappa carageenans, modified kappa carageenans, iota carageenans, modified iota carageenans, lambda carrageenan, and mixtures thereof. Carageenans suitable for use herein include those commercially available from the FMC Company under the series designation "Viscarin," including but not limited to Viscarin TP 329, Viscarin TP 388, and Viscarin TP 389.

The thickening agent can comprise one or more polymers. The polymer can be a polyethylene glycol (PEG), a polyvinylpyrrolidone (PVP), polyacrylic acid, a polymer derived from at least one acrylic acid monomer, a copolymer of maleic anhydride and methyl vinyl ether, a crosslinked polyacrylic acid polymer, of various weight percentages of the oral care composition as well as various ranges of average molecular ranges. Alternatively, the oral care composition can be substantially free of, essentially free of, or free of a copolymer of maleic anhydride and methyl vinyl ether.

The thickening agent can comprise one or more inorganic thickening agents. Some non-limiting examples of suitable inorganic thickening agents include colloidal magnesium aluminum silicate, silica thickeners. Useful silica thickeners include, for example, include, as a non-limiting example, an amorphous precipitated silica such as ZEODENT® 165 silica. Other non-limiting silica thickeners include ZEODENT® 153, 163, and 167, and ZEOFREE® 177 and 265 silica products, all available from Evonik Corporation, and AEROSIL® fumed silicas.

The oral care composition can comprise from 0.01% to about 15%, from 0.1% to about 10%, from about 0.2% to about 5%, or from about 0.5% to about 2% of one or more thickening agents.

Prenylated Flavonoids

The oral care composition of the present invention can comprise prenylated flavonoid. Flavonoids are a group of natural substances found in a wide range of fruits, vegetables, grains, bark, roots, stems, flowers, tea, and wine.

Flavonoids can have a variety of beneficial effects on health, such as antioxidative, anti-inflammatory, antimutagenic, anticarcinogenic, and antibacterial benefits. Prenylated flavonoids are flavonoids that include at least one prenyl functional group (3-methylbut-2-en-1-yl, as shown in Formula VIII), which has been previously identified to facilitate attachment to cell membranes. Thus, while not wishing to being bound by theory, it is believed that the addition of a prenyl group, i.e. prenylation, to a flavonoid can increase the activity of the original flavonoid by increasing the lipophilicity of the parent molecule and improving the penetration of the prenylated molecule into the bacterial cell membrane. Increasing the lipophilicity to increase penetration into the cell membrane can be a double-edged sword because the prenylated flavonoid will tend towards insolubility at high Log P values (high lipophilicity). Log P can be an important indicator of antibacterial efficacy.

As such, the term prenylated flavonoids can include flavonoids found naturally with one or more prenyl functional groups, flavonoids with a synthetically added prenyl functional group, and/or prenylated flavonoids with additional prenyl functional groups synthetically added.

Formula VIII

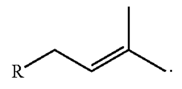

Prenyl Function Group with R representing the other portions of the molecule

Other suitable functionalities of the parent molecule that improve the structure-activity relationship (e.g., structure-MIC relationship) of the prenylated molecule include additional heterocycles containing nitrogen or oxygen, alkylamino chains, or alkyl chains substituted onto one or more of the aromatic rings of the parent flavonoid.

Flavonoids can have a 15-carbon skeleton with at least two phenyl rings and at least one heterocyclic ring. Some suitable flavonoid backbones can be shown in Formula IX (flavone backbone), Formula X (isoflavan backbone), and/or Formula XI (neoflavonoid backbone).

Formula IX

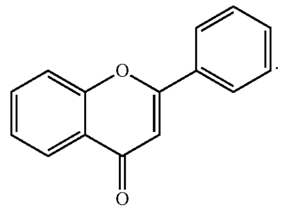

Flavone Backbone

Formula X

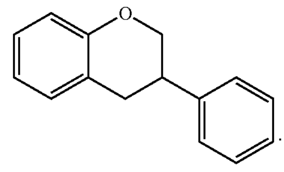

Isoflavan backbone

-continued

Formula XI

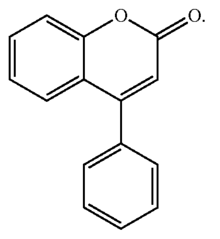

Neoflavanoid backbone

Other suitable subgroups of flavonoids include anthocyanidins, anthoxanthins, flavanones, flavanonols, flavans, isoflavonoids, chalcones and/or combinations thereof.

Prenylated flavonoids can include naturally isolated prenylated flavonoids or naturally isolated flavonoids that are synthetically altered to add one or more prenyl functional groups through a variety of synthetic processes that would be known to a person of ordinary skill in the art of synthetic organic chemistry.

Other suitable prenylated flavonoids can include Bavachalcone, Bavachin, Bavachinin, Corylifol A, Epimedin A, Epimedin A1, Epimedin B, Epimedin C, Icariin, Icariside I, Icariside II, Icaritin, Isobavachalcone, Isoxanthohumol, Neobavaisoflavone, 6-Prenylnaringenin, 8-Prenylnaringenin, Sophoraflavanone G, (−)-Sophoranone, Xanthohumol, Quercetin, Macelignan, Kuraridin, Kurarinone, Kuwanon G, Kuwanon C, Panduratin A, 6-geranylnaringenin, Australone A, 6,8-Diprenyleriodictyol, dorsmanin C, dorsmanin F, 8-Prenylkaempferol, 7-O-Methylluteone, luteone, 6-prenylgenistein, isowighteone, lupiwighteone, and/or combinations thereof. Other suitable prenylated flavonoids include cannflavins, such as Cannflavin A, Cannflavin B, and/or Cannflavin C.

Preferably, the prenylated flavonoid has a high probability of having an MIC of less than about 25 ppm for *S. aureus*, a gram-positive bacterium. Suitable prenylated flavonoids include Bavachin, Bavachinin, Corylifol A, Icaritin, Isoxanthohumol, Neobavaisoflavone, 6-Prenylnaringenin, 8-Prenylnaringenin, Sophoraflavanone G, (−)-Sophoranone, Kurarinone, Kuwanon C, Panduratin A, and/or combinations thereof.

Preferably, the prenylated flavonoid has a high probability of having an MIC of less than about 25 ppm for *E. coli*, a gram-negative bacterium. Suitable prenylated flavonoids include Bavachinin, Isoxanthohumol, 8-Prenylnaringenin, Sophoraflavanone G, Kurarinone, Panduratin A, and/or combinations thereof.

Approximately 1000 prenylated flavonoids have been identified from plants. According to the number of prenylated flavonoids reported before, prenylated flavonones are the most common subclass and prenylated flavanols is the rarest sub-class. Even though natural prenylated flavonoids have been detected to have diversely structural characteristics, they have a narrow distribution in plants, which are different to the parent flavonoids as they are present almost in all plants. Most of prenylated flavonoids are found in the following families, including Cannabaceae, Guttiferae, Leguminosae, Moraceae, Rutaceae and Umbelliferae. Leguminosas and Moraceae, due to their consumption as fruits and vegetables, are the most frequently investigated families and many novel prenylated flavonoids have been explored. *Humulus lupulus* of the Cannabaceae include 8-prenylnaringenin and xanthohumol, which play an important role in the health benefits of beer. The prenylated flavonoid can be incorporated through the hops extract, incorporated in a separately added extract, or added as a separate component of the oral care compositions disclosed herein.

Other Ingredients

The oral care composition can comprise a variety of other ingredients, such as flavoring agents, sweeteners, colorants, preservatives, buffering agents, or other ingredients suitable for use in oral care compositions, as described below.

Flavoring agents also can be added to the oral care composition. Suitable flavoring agents include oil of wintergreen, oil of peppermint, oil of spearmint, clove bud oil, menthol, anethole, methyl salicylate, eucalyptol, *cassia,* 1-menthyl acetate, sage, eugenol, parsley oil, oxanone, alpha-irisone, marjoram, lemon, orange, propenyl guaethol, cinnamon, vanillin, ethyl vanillin, heliotropine, 4-cis-heptenal, diacetyl, methyl-para-tert-butyl phenyl acetate, and mixtures thereof. Coolants may also be part of the flavor system. Preferred coolants in the present compositions are the paramenthan carboxyamide agents such as N-ethyl-p-menthan-3-carboxamide (known commercially as "WS-3") or N-(Ethoxycarbonylmethyl)-3-p-menthanecarboxamide (known commercially as "WS-5"), and mixtures thereof. A flavor system is generally used in the compositions at levels of from about 0.001% to about 5%, by weight of the oral care composition. These flavoring agents generally comprise mixtures of aldehydes, ketones, esters, phenols, acids, and aliphatic, aromatic and other alcohols.

Sweeteners can be added to the oral care composition to impart a pleasing taste to the product. Suitable sweeteners include saccharin (as sodium, potassium or calcium saccharin), cyclamate (as a sodium, potassium or calcium salt), acesulfame-K, thaumatin, neohesperidin dihydrochalcone, ammoniated glycyrrhizin, dextrose, levulose, sucrose, mannose, sucralose, *stevia*, and glucose.

Colorants can be added to improve the aesthetic appearance of the product. Suitable colorants include without limitation those colorants approved by appropriate regulatory bodies such as the FDA and those listed in the European Food and Pharmaceutical Directives and include pigments, such as $TiO_2$, and colors such as FD&C and D&C dyes.

Preservatives also can be added to the oral care compositions to prevent bacterial growth. Suitable preservatives approved for use in oral compositions such as methylparaben, propylparaben, benzoic acid, and sodium benzoate can be added in safe and effective amounts.

Titanium dioxide may also be added to the present composition. Titanium dioxide is a white powder which adds opacity to the compositions. Titanium dioxide generally comprises from about 0.25% to about 5%, by weight of the oral care composition.

Other ingredients can be used in the oral care composition, such as desensitizing agents, healing agents, other caries preventative agents, chelating/sequestering agents, vitamins, amino acids, proteins, other anti-plaque/anti-calculus agents, opacifiers, antibiotics, anti-enzymes, enzymes, pH control agents, oxidizing agents, antioxidants, and the like.

EXAMPLES

The invention is further illustrated by the following examples, which are not to be construed in any way as imposing limitations to the scope of this invention. Various other aspects, modifications, and equivalents thereof which, after reading the description herein, may suggest themselves to one of ordinary skill in the art without departing from the spirit of the present invention or the scope of the appended claims.

Experimental Methods

Acid Production and Acid Inhibition [%]

Acid production and acid inhibition were determined with the in vitro plaque glycolysis model (iPGRM). The purpose of this technique is to provide a simple and quick method for determining if compounds have an influence on the metabolic pathways that plaque microorganisms utilize to produce toxins that adversely affect gingival health.

The in vitro plaque glycolysis model (iPGRM) is a technique in which plaque is grown from human saliva and treated with various agents to determine anti-glycolytic activity of treatments. When bacteria convert sugar into energy with the help of enzymes, acids are formed. These acids demineralize and damage the dental enamel. The purpose of this technique is to provide a simple and quick method for determining if treatment compounds have an inhibitory effect on the metabolic pathways that plaque microorganisms utilize for the production of acids or toxins and/or inhibit their growth. For the purposes of the work here, if the test therapeutic compositions contain Sn, the Sn placebo should be tested. Additionally, the antibacterial composition should be tested with respect to its placebo to determine the iPGRM value for the antibacterial composition only. This is important if buffers, e.g., bicarbonate, orthophosphate, calcium carbonate, are present in the composition in addition to the antibacterial composition.

A plaque biofilm was grown on glass rods from fresh pooled human saliva and Trypticase Soy Broth (TSB) at 37° C. over 2 days by dipping glass rods into and out of media in a reciprocating motion. Treatments were 2 minutes of dentifrice slurry in water (1:5) or diluted treatment in water (1:5). After treatments, biofilms were incubated with TSB and sucrose until pH indicator showed a color change (~6 hrs). The pH of the media solutions was then measured to determine the amount of glycolysis inhibition relative to a negative control.

On Day 1, new glass rods (5 mm×90 mm) were polished approximately 25 mm from the un-tapered end on a lathe with silicon carbide paper of 240, 320, 400, and 600 grit used sequentially. After the initial polishing, the rods should be polished with 600 grit paper before each test. After polishing, rods were stored until ready to run test. Enough rods should be polished for a full rack of treatments. A rack can treat 12 compositions with 4 replicates of each composition such that the rack has 48 rods.

On Day 2, saliva was collected daily during the test from a panel of 5-10 people by paraffin stimulation and was refrigerated at 4° C. until it was needed throughout the day. Pool saliva carefully (do not pour in wax/mucus) and mix thoroughly before use. The rods were removed from storage, rinsed with deionized water to remove any sanding residue, disinfected in 70% ethanol/water solution, and were allowed to dry on a sterile surface. Subsequently, the rods were loaded into a hanging rack of holders that were used to dip the rods continuously into media vials containing growth media. The rod heights were adjusted and each rod was secured in place using a rubber O-ring. In the early afternoon, 7 mL of growth media (160 g of a solution of 3% TSB with 3% sucrose was mixed with 240 g pooled human saliva. This TSB/sucrose solution should be sterilized by autoclave before combining with the pooled human saliva.) into media vials. The media vials were arranged under the hanging rods on a rack in an incubation oven. The incubator has been previously modified such that a dipping motor can dip the rods into the media vials submerging 1.5 cm of the rod into the growth media at a frequency of 1 dip per minute without the rods touching the walls of the media vial. The rods were dipped overnight this way.

On Day 3, an enriched growth media was prepared (500 g of a solution of 3% TSB and 10% sucrose was mixed with 33 g pooled human saliva. This TSB/sucrose solution should be sterilized by autoclave before combining with the pooled human saliva.). This enriched growth media was pipetted into a new set of media vials (7 mL per vial) and was swapped for the overnight growth media from Day 1. The rods were dipped throughout the day in this enriched growth media for 5 hours at 37° C. in the incubation oven. At the end of the day, a new overnight growth media was prepared (40 g of a solution of 3% TSB was mixed with 360 g pooled human saliva and 0.5 g sucrose), pipetted into a new set of media vials, and swapped for the enriched growth media. The rods were dipped overnight in the same fashion as on the first day.

On Day 4, a glycolysis media was prepared by combining 0.15 g TSB, 25 g sucrose, and 500 mL deionized water resulting in a solution of 0.03% TSB and 0.5% sucrose in water. This solution was mixed then sterilized in an autoclave. The pH was then adjusted to 6.5 using 0.1M HCl and pipetted into new media vials (7 mL). Two extra vials were filled than were needed for the rack of rods as pH blanks. Two drops of chlorophenol red solution were added to each of the 4 tubes that contained the negative control (Crest Cavity Protection slurry). Three drops of bromocresol purple solution were added to 2 tubes that contained the positive control (1% Chlorhexidine solution). Set the rack aside until treatments are complete. Vials were prepared containing 12 mL of deionized water to rinse off the treatments. Vials were prepared containing the treatment slurries/solutions (7 mL) of homogenized treatment and water. The rods were dipped into the treatment vials for 2 minutes, rinsed for 10 dips in a first set rinse vials, rinsed for 10 dips in a second set of rinse vials, rinsed for 10 dips in a third set of rinse vials, and returned to the incubator rack. The entire biofilm was treated and rinsed. Once all treatments were complete, the biofilms on the rods were fully submerged in the glycolysis media inside the incubation oven with no dipping for 2 hours. After two hours, the dipping apparatus was activated. The total incubation time was between 3 to 7 hours. Incubation is terminated when the pH value in the glycolysis media of the negative controls is between 4.8-5.6, more ideally 4.9-5.2, and when the pH value in the glycolysis media of the positive controls is above the negative control. If the indicator dye in the positive control turns yellow, i.e., the pH has dropped beneath 5.2, the incubation has gone on too long and the test will need to be repeated.

After incubation termination on Day 4, the rods were removed from the glycolysis media and allowed to dry in the oven. The glycolysis media was removed from the incubation oven, allowed to return to room temperature, and the pH was measured in each vial and the blank vials to determine the average pH change of the media following treatment. The change in pH is determined with respect to the blank vials. If the final pH of the blank is less than 6.6, the test needs to be repeated. If the difference between the positive and negative control is not significant in a student's t-test, the test needs to be repeated. If the change in pH of the negative control with respect to the blank is less than 1, the test needs to be repeated.

After the pH values of all the vials were measured, the ΔpH per vial was determined by subtracting its pH from the average pH of the blanks. The glycolysis inhibition efficacy is determined from the following formula. The average ΔpH of a treatment was determined by averaging the results from the four replicate vials per treatment.

$$\text{Acid Inhibition (\%)} = 100 - \left(\frac{Avg\Delta pH_{sample}}{Avg\Delta pH_{neg\ ctrl}}\right) \times 100 \quad \text{Formula 2}$$

If the efficacy of the positive control (1% Chlorhexidine solution) is not between about 65% to about 85% with respect to the negative control (Crest Cavity Protection, Procter & Gamble, Cincinnati, OH), the test was repeated.

Anticavity Activity

The test design used here is similar to those found in the FDA Method #37 of the Fluoride Anti-Caries OTC Monograph. The major variations are the diet used (MIT 200 rather than #469), the caries score method (Keyes method rather than HMA), and treatment frequency. Experimental procedures were conducted according to the FDA regulations Part 58.

Using litters as a covariate, the use of between 50 and 58 (depending on the type of fluoride) animals per treatment group satisfies the most stringent power requirements of the ADA's Council on Dental Therapeutics 20% clinical difference between treatments at 80% power. However, we have been routinely using 40 animals per treatment group and both the ADA's CDT and the FDA have consistently accepted these tests. This requires initiating the study with 40 animals per group. Twenty-three (23) litters provided these animals. When studies are sized as such, treatment differences of approximately 16% have been found to be significant on occasion, thus is generally considered the cusp of clinical significance.

All protocols are reviewed and approved by the Institutional Animal Care and Use Committee prior to the receipt of animals.

The animals were weanling mixed-sex Sprague Dawley rats; weighing 29-53 grams. Due to the shipping schedule of the supplier, the dams were received with their entire birth litter. The litters were received when the pups were 6 days of age and litter size was reduced at 8 days of age to ten (10) pups per litter. Twenty-five (25) litters were purchased. The five extra litters were to allow for any mortality prior to stratification. Any unused animals were euthanized after the study stratification.

The litters were maintained in large solid-bottom (box-type) cages with dams until the pups were weaned at 18 days of age. Starting at 9 days of pup age, the dams were rotated daily among the litters until the pups were weaned at 18 days of age. The pups were maintained in the box cages until 21 days of age. At that time, the pups were stratified and housed in pairs in suspended wire-bottomed cages that had been cleaned and sanitized prior to usage. The change in caging was required to prevent artificially increasing the caries rate due to direct contact bedding. The cages were arranged so that all animals of the individual groups were together and the cages were labeled with group designation and treatment (treatment code) that the animals received.

When the pups were 21 days of age they were given unique numbers by ear-punch with records kept of litter-mates. Animals were assigned to groups in such a manner that groups were balanced for litter, weight and sex. There were 40 animals per group.

Upon receipt, dams and litters were provided rodent lab diet until the pups were 8 days of age. On day 8 (pup age) dams and litters were provided Diet MIT 305. Pups were provided Diet MIT 200 *ad libitum* at day 18 (pup age) and throughout the test period. All animals were provided with deionized water *ad libitum*.

Box caging was changed at day 13 and again at day 18 of pup age. Following administration of the inoculum, box cages and the bedding were decontaminated by autoclaving prior to sanitizing. Cage boards were changed three times a week at the time when fresh food and water were given (Monday, Wednesday and Friday). Clean and sanitized water bottles and food jars were provided weekly. Suspended caging and banks were sanitized bi-weekly. The animals were observed daily by a staff member and weekly by the attending veterinarian for any signs of health problems. The animals were housed in an AAALAC-accredited facility. Room temperature was maintained at 72° F. (±6° F.) with 10-15 air changes per hour and a 12-hour light cycle.

On day 15 (pup age), the animals received an oral inoculation of streptomycin-resistant *S. sobrinus* 6715 (ATCC strain #27352) culture. This involved flooding the mouth with 0.2 ml of culture/animal. On day 18 (pup age) the animals were inoculated with *S. sobrinus* for three consecutive days (age 18, 19 and 20 days). This involved placing 0.1 ml of the *S. sobrinus* culture on the occlusal surfaces of each of the mandibular molar quadrants, putting 10 cc of this concentration-adjusted culture into each sanitized and filled water bottle, and lightly spraying the bedding with no more than 10 cc of the remaining culture. All water bottles were removed and sanitized 24 hours after inoculum has been added. The inoculums were administered to the animals with a 200 micropipette.

The treatment phase began at day 22 of pup age. Each treatment had a labeled plastic beaker that was designated for that treatment only. Fresh materials (i.e., obtained from the stock supply) were used for each treatment. The dentifrices were mixed in a 1:1 ratio (by weight) with deionized water. Specifically, 10 grams of dentifrice was weighed into a 30 ml beaker; 10 grams of deionized water was then added to the dentifrice. The mixture was then stirred by hand (30 seconds) with a clean micro spatula for the purpose of creating a smooth mixture. The beaker containing the slurry and a small magnetic stirring bar was placed on a magnetic stirrer, which was set at the lowest speed and allowed to stir for four (4) minutes prior to treatment. The slurry was prepared immediately prior to each treatment.

A cotton-tipped applicator was dipped into the slurry (for 2 seconds) and was applied to one-half of the rat's mouth in such a way that the sides of the applicator came into contact with both the mandibular and maxillary molars on one side of the mouth. The treatment was accomplished by using a rolling motion of the sides of the applicator over the mandibular and maxillary molar teeth for 15 seconds. The applicator was dipped into the slurry for the second time (again, for 2 seconds) and the other side of the rat's mouth similarly treated for 15 seconds. A new applicator was used for each animal.

Treatments were administered twice daily for five days with a single daily treatment on weekends. The first treatment each day began at approximately the same time every day, and the second treatment did begin no earlier than six hours after the first treatment. Singular treatments were given at a 24-hour interval on weekends. Treatment materials were stored at room temperature. All treatment products were returned to sponsor at study completion.

One week after the initiation of the inoculation regimen and at study termination, an oral swabbing was taken from each rat using a sterile cotton swab (six-inch, single-tipped applicator). The microorganisms on the mandibular and maxillary molar teeth were sampled, using a rolling motion of the swab for 15 seconds on one side of the mouth, rolled over the tongue, and rolled over the molar teeth on the other side of the mouth for an additional 15 seconds. Immediately after the applicator was removed from the animal's mouth, it was streaked across half of a 100 mm petri plate containing *Mitis Salivarius* agar to which 200 units/ml of streptomycin sulfate was added. The plates were incubated for 48 hours at 37° C. with 10% $CO_2$. The colony count taken after the 48 hours of incubation was recorded in the logbook.

The experimental duration of the rat caries studies is three weeks. Immediately prior to termination, all animals were observed for any visual signs of ill health or pathology, individually weighed and an oral swabbing taken to confirm *S. sobrinus* implantation. The animals were euthanized by carbon dioxide inhalation. Code numbers were assigned to each animal and the heads were then removed, placed in individual jars along with the code number, and cooked under pressure (10 PSI for 12 minutes). The hemijaws were then removed and freed of all soft tissue.

The cleaned hemijaws (four quadrants) were put into plastic vials with the code numbers taped to the vial. A murexide solution (0.3 g murexide; 300 ml DI H20 and 700 ml of ethanol) was added to each vial and the jaws were allowed to stain overnight. The jaws were then rinsed and allowed to air dry.

The hemijaws were microscopically examined for smooth surface caries, sectioned, and then microscopically examined for sulcal and interproximal caries using the Keyes Method. The scoring method is detailed in Navia, J N, *Animal Models in Dental Research*, pp 287-290, 1977; and Keyes, PH, J. Dent. Res. 37:1088-1099, 1958. All analyses were performed using SAS statistical software, version 9.4. The groups were compared using analysis of variance (ANOVA), with a fixed effect for group and a random effect for litter. The litter effect was included in the models to reduce a known factor affecting the variability of the measurements. Pair-wise comparisons between groups were made using Tukey's multiple comparisons procedure to control the overall significance level ($\alpha$=0.05) of the comparisons.

The specific types of data, which were tabulated, and statistically analyzed may include:

1) Mortality Data Experimental Phase
   - a. Initial number of animals
   - b. Final number of animals
   - c. Percent mortality
2) Growth Data Experimental Phase
   - a. Initial body weight (mean±S.E.M.)
   - b. Final body weight (mean±S.E.M.)
3) Caries Experience
   - a. Enamel and dentinal involvement of smooth surface (buccal, lingual) lesions (mean±S.E.M.)
   - b. Enamel and dentinal involvement of interproximal lesions (mean±S.E.M.)
   - c. Enamel and dentinal involvement of total smooth surface (buccal, lingual & interproximal) lesions (mean±S.E.M.)
   - d. Enamel and dentinal involvement of sulcal lesions (mean±S.E.M.)
   - e. Total caries involvement combining the scores from the Keyes method of scoring smooth surface, interproximal, and sulcal caries (mean±S.E.M.)

Preparation of Oral Care Compositions

The oral care compositions of TABLE 1A were prepared by combining one or more humectants, water, sweetener(s), tin ion source, sodium gluconate, and/or flavor(s) to create a liquid mixture. The liquid mixture was homogenized at 25° C. for 2 minutes. Next, sodium hydroxide (50% solution) was added to the liquid mixture and the liquid mixture was homogenized at 25° C. for 2 minutes. A separate powder mixture was prepared by combining a portion of the calcium ion source and any thickening agents, such as xanthan gum and/or sodium carboxymethylcellulose. The powder mixture was then combined with the liquid mixture. Next, the surfactant, such as sodium lauryl sulfate, was added to the mixture. The contents were homogenized at 25° C. for 2 minutes. The hops extract was then combined with the mixture and homogenized at 25° C. for 2 minutes. Finally, the remaining portion of the calcium ion source and the buffering agent were combined with the mixture and homogenized at 25° C. for 2 minutes.

Preparation of Commercial Oral Care Compositions with Hops Beta Acid

The commercial oral care compositions were combined with hops beta acid extract or hops total extract by weighing out a portion of commercial oral care composition and mixing in the appropriate amount of hops extract. The combined oral care composition was homogenized at 25° C. for at least 2 minutes.

TABLE 1A

| Oral Care Compositions | | | |
|---|---|---|---|
| | Formula A | Formula B | Formula C |
| Glycerin | 49.10 | 47.80 | — |
| Sorbitol | — | — | 37.98 |
| Water | — | — | 13.00 |
| Sodium Monofluorophosphate | — | 1.15 | — |
| Sodium Gluconate | 1.00 | 1.00 | 1.00 |
| $SnCl_2$ | 1.10 | 1.10 | 1.10 |
| $CaCO_3$ | 32.00 | 32.00 | 32.00 |
| Xanthan Gum | 0.50 | 0.50 | 0.30 |
| Carboxymethylcellulose | — | — | 1.00 |
| Carbomer | 1.00 | 1.00 | — |
| Sodium Lauryl Sulfate | 1.40 | 1.40 | 1.29 |
| Flavor | 1.00 | 1.00 | 1.00 |
| Sodium Saccharin | 0.40 | 0.40 | 0.50 |
| Stevia Glycosides | 0.30 | 0.30 | — |
| Sodium Hydroxide | 1.20 | 1.35 | 0.33 |
| Hops Beta Acid Extract* | 0.50 | 0.50 | 0.50 |
| Sodium Bicarbonate | 10.00 | 10.00 | 10.00 |
| Titanium Dioxide | 0.50 | 0.50 | — |

*Hops Beta Acid Extract supplied by Hopsteiner ®, with 45% hops beta acids and less than 1% hops alpha acids Formula A, B, and C, as shown in TABLE 1A, were prepared in accordance with the Experimental Methods, described above. The Hops Beta Acids were supplied by Hopsteiner® as an extract from *Humulus lupulus*. The Hopsteiner® extract was approximately 45%, by weight of the extract, of hops beta acids and less than 1%, by weight of the extract, of hops alpha acids. Formula A and B have hops beta acids with no independently added water. Formula A and B differ only in that Formula B includes a fluoride ion source (sodium monofluorophosphate, NaMFP), which was used in the total enamel caries test shown in TABLE 4. Formula C include hops beta acids without fluoride in a high-water chassis.

TABLE 1B

| Hops Beta Acids Extract Specification | |
|---|---|
| Ingredient | Amount (wt %) |
| Hops Beta Acids | 45 ± 2 |
| Hops Alpha Acids | 0.4 ± 0.3 |
| Hops oils | 1.5 ± 0.5 |
| Propylene Glycol | 20 ± 15 |
| Water | <8% |
| pH | 11 ± 0.5 |

TABLE 1B describes the hops beta acid extract provided by Hopsteiner®. Since the hops beta acids are provided as an extract, there can be some variability in the amounts of certain ingredients. However, the extract comprises approximately 45%, by weight of the extract, of the hops beta acids and approximately 0.4%, by weight of the extract, of hops alpha acids. This is dramatically different to previous hops extracts which typically have more hops alpha acids than hops beta acids. Other minor ingredients may be present in the Hops Beta Acid extract.

TABLE 2

Acid Production and Glycolysis Inhibition [%] after treatment of 3-day biofilm

| | Acid Production (ΔpH) | | Mean Acid Inhibition (%) | |
|---|---|---|---|---|
| Treatment | Mean | SE | Mean | SE |
| Crest ® Cavity Protection (NaF) | 1.56 | 0.08 | 0 | 1.67 |
| Crest ® Pro-Health ™ Advanced ($SnF_2$) | 0.80 | 0.16 | 48.72 | 3.43 |
| Crest ® Gum Care ($SnF_2$ + $SnCl_2$) | 0.53 | 0.05 | 66.03 | 1.05 |
| 1% Chlorhexidine | 0.30 | 0.07 | 80.77 | 1.55 |
| Formula A (Hops Beta Acids + $SnCl_2$) | 0.10 | 0.05 | 93.59 | 1.05 |
| Formula B (Hops Beta Acids + $SnCl_2$ + NaMFP) | 0.07 | 0.16 | 95.51 | 0.98 |

TABLE 2 displays the change in acid production in a 3-day biofilm using the iPGRM test described herein. After treatment with a commercial Crest® toothpaste containing sodium fluoride, the acid product mean is 1.56 with a mean inhibition of 0% as the negative control. Treatment of the 3-day biofilm with a Crest® toothpaste containing stannous fluoride resulted in decreases in acid production and a net mean acid inhibition of 48.72% (Crest® Pro-Health™) and 66.03% (Crest® Gum Care). This was an expected result as the stannous ion is known to act as an antibacterial, which can lower the number of bacteria producing acid in the biofilm. Crest® Gum Care performed slightly better than Crest® Pro-Health™ due to additional amounts of stannous ions (i.e. $SnCl_2$). Chlorhexidine is an antibacterial agent that can be prescribed to treat gingivitis. Treatment with chlorhexidine resulted in a mean acid inhibition of 80.77%, which was not unexpected because chlorhexidine is known as an extremely effective antibacterial agent.

TABLE 2 also shows that Formula A (93.59%) and B (95.51%) displayed essentially zero acid production with a mean acid inhibition of approximately 100%. It was unexpected that Formula A and B (with a fluoride ion source) would be essentially 100% effective at preventing acid production given fluoride and/or chlorhexidine alone, two of the most prevalent and effective antibacterial agents, do not produce nearly 100% acid inhibition.

TABLE 3

| Total Enamel Caries | | | |
|---|---|---|---|
| Treatment | Total Enamel Caries | % Positive Control | % Negative Control |
| Silica Placebo[a] | 38.70 ± 2.06 | 47 | 0 |
| Silica + NaMFP[b] | 31.55 ± 2.08 | 75 | 19 |
| Crest ® Cavity Protection[c] | 25.28 ± 1.99 | 100 | 35 |
| Formula A | 26.23 ± 2.01 | 96 | 32 |
| Formula B | 20.25 ± 1.91 | 125 | 48 |

[a]Silica placebo is the negative control without any fluoride ion source
[b]NaMFP at 1000 ppm
[c]NaF 1100 ppm + Silica is the positive control with silica and a fluoride ion source TABLE 3 displays the results from the rat caries test, FDA No. 37. The rat caries test is a biological test method required by the U.S. FDA monograph to show efficacy of an anticaries drug, currently including only fluoride ion sources. As shown in TABLE 3, the negative control, Silica Placebo, is a toothpaste with silica abrasive, but not any fluoride ion source. Silica+NaMFP is a USP NaMFP toothpaste with sodium monofluorophosphate and a silica abrasive. Crest® Cavity Protection is a toothpaste with sodium fluoride and a silica abrasive. In contrast, Formula A has no fluoride ion source or silica abrasive, but has hops beta acids and stannous chloride. Unexpectedly, Formula A (26.23), without any fluoride ion source, performed similar to the Crest® Cavity Protection (25.28), a dentifrice with 1100 ppm sodium fluoride. Additionally, Formula A performed better than a dentifrice with sodium monofluorophosphate with silica abrasive (26.23 for Formula A vs. 31.55 for NaMFP). The only anticaries drug listed in the U.S. FDA monograph are stannous fluoride, sodium fluoride, and sodium monofluorophosphate. In other words, Formula A is a fluoride-free anticavity toothpaste.

Additionally, Formula B (125% of the positive control) performed even better than any of the tested anticaries drug, including Crest Cavity protection. Additionally, a comparative toothpaste with sodium monofluorophosphate, but without hops beta acids, had a total enamel caries of 31.55 while Formula B with 0.5% wt of hops beta acids had a total enamel caries effect of 20.25, which was a huge and unexpected improvement. Hops beta acids and fluoride ion sources likely act with different, but complementary mechanisms to prevent caries formation in tooth enamel.

TABLE 4

Final pH, Acid Production and Glycolysis Inhibition [%] after treatment of 3-day biofilm

| | Key Ingredients | Acid Production (ΔpH) | | Acid Inhibition (%) | |
|---|---|---|---|---|---|
| Treatment | (wt %) | Mean | SD | Mean | SD |
| Colgate Total[SF] + 0.5 wt % Hops Beta Acid Extract | 0.454% $SnF_2$ Pyrophosphate ZnPhosphate ~30% water | 0.22 | 0.02 | 87.5 | 0.89 |

TABLE 4-continued

Final pH, Acid Production and Glycolysis Inhibition [%] after treatment of 3-day biofilm

| Treatment | Key Ingredients (wt %) | Acid Production (ΔpH) Mean | SD | Acid Inhibition (%) Mean | SD |
|---|---|---|---|---|---|
| Colgate Total$^{SF}$ 0.64 wt % Hops Total Extract | 0.454% $SnF_2$ Pyrophosphate ZnPhosphate ~30% water | 1.23 | 0.01 | 30.2 | 0.84 |
| Colgate Total$^{SF}$ | 0.454% $SnF_2$ Pyrophosphate ZnPhosphate ~30% water | 1.07 | 0.04 | 39.0 | 1.99 |
| Parodontax + 0.5 wt % Hops Beta Acid Extract | 0.454% $SnF_2$ Tripolyphosphate No Added Water | 0.25 | 0.01 | 85.9 | 0.75 |
| Parodontax + 0.64 wt % Hops Total Extract | 0.454% $SnF_2$ Tripolyphosphate No Added Water | 1.32 | 0.05 | 25.1 | 2.78 |
| Parodontax | 0.454% $SnF_2$ Tripolyphosphate No Added Water | 1.38 | 0.01 | 21.2 | 0.49 |
| Formula D + 0.5 wt % Hops Beta Acid Extract | 0.454% $SnF_2$ $SnCl_2$ ZnCitrate | 0.18 | 0.02 | 89.9 | 1.10 |
| Formula D + 0.64 wt % Hops Total Extract | 0.454% $SnF_2$ $SnCl_2$ ZnCitrate | 1.10 | 0.02 | 37.6 | 1.21 |
| Formula D | 0.454% $SnF_2$ $SnCl_2$ ZnCitrate | 1.04 | 0.02 | 40.7 | 1.05 |
| Crest ® Gum Care | 0.454% $SnF_2$ $SnCl_2$ | 0.94 | 0.03 | 46.7 | 1.59 |
| Crest ® Pro-Health ™ Advanced | 0.454% $SnF_2$ | 1.19 | 0.09 | 32.3 | 4.85 |
| Crest ® Cavity Protection | 0.32% NaF | 1.76 | 0.06 | 0.00 | 3.21 |

TABLE 5

Final pH, Acid Production and Glycolysis Inhibition [%] after treatment of 3-day biofilm

| Treatment | Key Ingredients (wt %) | Acid Production (ΔpH) Mean | SD | Acid Inhibition (%) Mean | SD |
|---|---|---|---|---|---|
| Colgate Total + 0.5 wt % Hops Beta Acid Extract | 0.32% NaF L-Arginine Zn Citrate/ Zn Oxide | 0.31 | 0.02 | 83.8 | 1.07 |
| Colgate Total + 0.64 wt % Hops Total Extract | 0.32% NaF L-Arginine Zn Citrate/ Zn Oxide | 1.54 | 0.07 | 19.6 | 3.56 |
| Colgate Total | 0.32% NaF L-Arginine Zn Citrate/ Zn Oxide | 1.43 | 0.10 | 25.2 | 5.49 |
| Colgate Max Cavity + 0.5 wt % Hops Beta Acid Extract | 1.1% MFP L-Arginine $CaCO_3$ abrasive | 0.22 | 0.01 | 88.6 | 0.65 |
| Colgate Max Cavity + 0.64 wt % Hops Total Extract | 1.1% MFP L-Arginine $CaCO_3$ abrasive | 1.72 | 0.05 | 9.9 | 2.48 |
| Colgate Max Cavity | 1.1% MFP L-Arginine $CaCO_3$ abrasive | 1.65 | 0.01 | 14.0 | 0.66 |

TABLE 5-continued

Final pH, Acid Production and Glycolysis Inhibition [%] after treatment of 3-day biofilm

| Treatment | Key Ingredients (wt %) | Acid Production (ΔpH) Mean | SD | Acid Inhibition (%) Mean | SD |
|---|---|---|---|---|---|
| Crest ® Gum Care | 0.454% $SnF_2$ | 1.34 | 0.03 | 29.9 | 1.75 |
| Crest ® Pro-Health ™ Advanced | 0.454% $SnF_2$ | 1.42 | 0.04 | 25.6 | 2.06 |
| Crest ® Cavity Protection | 0.32% NaF | 1.91 | 0.02 | 0.00 | 1.21 |

TABLE 4 and TABLE 5 show that hops beta acid, can be added to any toothpaste and provide additional benefits, including toothpastes with a variety of active agents, abrasives, water levels, polyphosphate, etc. Hops beta acid can be added to toothpastes including stannous fluoride, stannous chloride, sodium fluoride, silica, calcium carbonate, polyphosphate, amino acids, such as arginine, and/or zinc. As shown in TABLE 4 and TABLE 5, the addition of hops beta acid improves the antibacterial performance of any oral care composition by the iPGRM test method. Importantly, the antibacterial performance was not improved through the addition of a hops extract that included both hops alpha acid and hops beta acid. In fact, the extract including both hops alpha extract and hops beta extract, the "hops total extract," decreased the antibacterial performance in many cases.

The hops beta extract used was the hops beta extract of TABLE 1B. The hops total extract included hops alpha acid and hops beta acid. The Hops Alcohol-Free Liquid Extract ("hops total extract") was purchased from Hawaii Pharm and used as is. Hops beta acid extract was added at 0.5 wt % and the hops total extract was added at 0.64 wt %. In all cases, the amount of hops acid (either hops alpha acid+hops beta acid or essentially solely hops beta acid) were essentially equivalent at approximately 0.23%.

For example, the hops beta acid extract and hops total extract were added to Colgate Total$^{SF}$, which included stannous fluoride as an antigingivitis agent, pyrophosphate, and at least 30 wt % of water, as shown in TABLE 4. The addition of the hops beta acid extract to Colgate Total$^{SF}$ improved the acid inhibition from 39.0% to 87.5%. In contrast, the addition of hops total extract to Colgate Total$^{SF}$ decreased the acid inhibition from 39.0% to 30.2%

The hops beta acid extract and the hops total extract were added to Colgate Total, which included sodium fluoride, arginine, zinc citrate, zinc oxide, and a calcium carbonate abrasive, as shown in TABLE 5. The addition of the hops beta acid extract to Colgate Total improved the acid inhibition from 25.2% to 83.8%. In contrast, the addition of hops total extract to Colgate Total decreased the acid inhibition from 25.2% to 19.6%.

The hops beta acid extract and the hops total extract were added to Parodontax, which included stannous fluoride, tripolyphosphate, and no added water, as shown in TABLE 4. The addition of the hops beta acid extract to Parodontax improved the acid inhibition from 21.9% to 85.9%. The addition of the hops total extract to Parodontax only marginally improved the acid inhibition from 21.9% to 25.1%.

The hops beta acid extract and the hops total extract were added to Formula D, which included stannous fluoride, stannous chloride, and zinc citrate. The addition of the hops beta acid extract to Formula D improved the acid inhibition from 40.7% to 89.9%. The addition of the hops total extract to Formula D decreased the acid inhibition from 40.7% to 37.6%.

The hops beta acid extract and the hops total extract were added to Colgate Max Cavity, which included sodium fluoride and silica. The addition of the hops beta acid extract to Colgate Max Cavity improved the acid inhibition from 14.0% to 88.6%. The addition of the hops total extract to Colgate Max Cavity decreased the acid inhibition from 14.0% to 9.9%. In the other formulas where hops was added, the average effect of the hops was an additional 60% acid inhibition. However, in the Colgate Max Cavity formula with hops, the additional benefit was nearly 75%, a 15% increase in acid inhibition. The Colgate Max Cavity formula has the basic amino acid, arginine. It is well known that arginolytic bacteria that can consume arginine would nevertheless prefer to consume sugar and make acid in the presence of a sugar source and at low pH, namely the conditions of the iPGRM used here. Therefore, in order for bacteria to effectively utilize arginine to produce ammonia and neutralize acid-forming biofilms, it is required that the biofilm pH be maintained at quite a high level already. This tends to impede arginine's effectiveness in biofilms where sugar is present and the pH is low. As demonstrated in TABLE 5, hops activates that arginolytic bacterial pathway by preventing the pH from falling in the presence of sugar. This, unexpectedly, produced a synergistic effect and resulted in a more effectively stabilized biofilm pH than either ingredient could achieve on its own.

Thus, hops beta acids are an extremely effective antibacterial agent, which can improve existing dentifrice formulations regardless of chassis. Hops beta acids can improve antibacterial activity in dentifrice compositions comprising sodium fluoride, sodium monofluorophosphate, and/or stannous fluoride. Hops beta acids can improve antibacterial activity in dentifrice compositions that are anhydrous, low water, moderate water, or high water formulations. Hops beta acids can improve antibacterial activity in dentifrice compositions comprising one or more polyphosphates. Hops beta acids can improve antibacterial activity in dentifrice compositions comprising a silica abrasive and/or a calcium abrasive, such as calcium carbonate. Hops beta acids can improve antibacterial activity in dentifrice compositions comprising a basic amino acid, such as arginine. Hops beta acids can improve antibacterial activity in dentifrice compositions comprising a tin ion source, a zinc ion source, or combinations of tin and zinc ions. Importantly, these benefits were not found when a total extract (i.e. one with hops alpha acid and hops beta acid) was used.

Thus, described herein are oral care compositions with a mean acid inhibition of at least 50%, at least 55%, at least 60%, at least 70%, or at least 80%, upon the addition of hops beta acid, either through a hops beta acid extract, a direct addition of one or more hops beta acids, or any other suitable source of hops beta acid.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An oral care composition comprising:

(a) hops extract comprising hops beta acid and hops alpha acid, wherein the hops extract comprises greater than 0% to less than 5%, by weight of the hops extract, of the hops alpha acids, wherein the oral care composition comprises about 0.01% to about 10%, by weight of the composition, of the hops beta acid, and wherein the hops beta acid comprises only non-hydrogenated hops beta acids; and (b) about 0.01% to about 10%, by weight of the composition, of fluoride, wherein the oral care composition has a pH of greater than 7.

2. The oral care composition of claim 1, further comprising about 10% to about 50%, by weight of the composition, of a calcium ion source.

3. The oral care composition of claim 2, further comprising about 1% to about 20%, by weight of the composition, of a buffering agent, wherein the buffering agent comprises a conjugate acid of the calcium ion source.

4. The oral care composition of claim 3, wherein the calcium ion source comprises calcium carbonate and the conjugate acid of the calcium ion source comprises a bicarbonate anion.

5. The oral care composition of claim 1, further comprising a calcium abrasive.

6. The oral care composition of claim 5, wherein the calcium abrasive comprises calcium carbonate.

7. The oral care composition of claim 1, wherein the composition is free of silica.

8. The oral care composition of claim 1, wherein the hops beta acid comprises lupulone, colupulone, adlupulone, or combinations thereof.

9. The oral composition of claim 1, wherein the fluoride is selected from the group consisting of sodium fluoride, sodium monofluorophosphate, amine fluoride, indium fluoride, and combinations thereof.

10. The oral care composition of claim 1, further comprising about 0.01% to about 10%, by weight of the composition, of an antibacterial agent comprising a metal ion source.

11. The oral care composition of claim 10, wherein the metal ion source comprises tin, zinc, or combinations thereof.

12. The oral care composition of claim 10, wherein the metal ion source comprises the tin, and the tin comprises stannous chloride.

13. The oral care composition of claim 1, further comprising potassium nitrate.

14. The oral care composition of claim 1, further comprising an amino acid.

15. The oral care composition of claim 14, wherein the amino acid comprises glycine, alanine, valine, isoleucine, tryptophan, phenylalanine, proline, methionine, leucine, serine, threonine, tyrosine, asparagine, glutamine, cysteine, citrulline, aspartic acid, glutamic acid, lysine, arginine, histidine, or combinations thereof.

16. The oral care composition of claim 1, further comprising about 0.01% to about 20%, by weight of the composition, of a thickening system, wherein the thickening system comprises polyacrylic acid, cellulose, a cellulose derivative, xanthan gum, a carrageenan, or combinations thereof.

* * * * *